US008609411B2

(12) United States Patent
Zhang et al.

(10) Patent No.: US 8,609,411 B2
(45) Date of Patent: Dec. 17, 2013

(54) EX VIVO EXPANSION OF HUMAN HEMATOPOIETIC STEM CELLS

(75) Inventors: ChengCheng Zhang, Irving, TX (US); Harvey Lodish, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 852 days.

(21) Appl. No.: 12/598,770

(22) PCT Filed: May 2, 2008

(86) PCT No.: PCT/US2008/062365
§ 371 (c)(1),
(2), (4) Date: Dec. 14, 2009

(87) PCT Pub. No.: WO2008/137641
PCT Pub. Date: Nov. 13, 2008

(65) Prior Publication Data
US 2011/0117061 A1 May 19, 2011

Related U.S. Application Data

(60) Provisional application No. 60/927,668, filed on May 4, 2007, provisional application No. 61/014,006, filed on Dec. 14, 2007.

(51) Int. Cl.
C12N 5/00 (2006.01)
(52) U.S. Cl.
USPC ............................ 435/375; 424/93.7; 435/325
(58) Field of Classification Search
None
See application file for complete search history.

(56) References Cited

U.S. PATENT DOCUMENTS

| 5,004,681 | A | 4/1991 | Boyse et al. |
| 5,061,620 | A | 10/1991 | Tsukamoto et al. |
| 5,681,559 | A | 10/1997 | DiGiusto et al. |
| 6,841,386 | B2 | 1/2005 | Kraus et al. |
| 7,282,201 | B2 | 10/2007 | Miura et al. |
| 7,767,453 | B2 | 8/2010 | Zhang et al. |
| 7,807,464 | B2 | 10/2010 | Zhang et al. |
| 8,372,638 | B2 | 2/2013 | Kiss |
| 2005/0032122 | A1 | 2/2005 | Hwang et al. |
| 2005/0153443 | A1* | 7/2005 | Lanza et al. ................. 435/366 |
| 2005/0276793 | A1 | 12/2005 | Milhem et al. |
| 2010/0261152 | A1 | 10/2010 | Riordan |

FOREIGN PATENT DOCUMENTS

| EP | 0 962 530 | 12/1999 |
| EP | 1 308 511 | 5/2003 |
| WO | WO 94/29438 | 12/1994 |
| WO | WO 95/03693 | 2/1995 |
| WO | WO 95/05843 | 3/1995 |
| WO | WO 95/08105 | 3/1995 |
| WO | WO 97/21824 | 6/1997 |
| WO | WO 97/21825 | 6/1997 |
| WO | WO 00/52167 | 9/2000 |
| WO | WO 02/083845 | 10/2002 |
| WO | WO 2006/127809 | 11/2006 |

OTHER PUBLICATIONS

Jang Y-Y et al. 2004. Hematopoietic stem cells convert into liver cells within days without fusion. Nature Cell Biology 6: 532-539.*
Antonchuk et al., "HOXB4-Induced Expansion of Adult Hematopoietic Stem Cells Ex Vivo," Cell, vol. 109, Issue 1, pp. 39-45 (Apr. 2002).
Arai et al., "Tie2/Angiopoietin-1 Signaling Regulates Hematopoietic Stem Cell Quiescence in the Bone Marrow Niche," Cell, vol. 118, pp. 149-161 (Jul. 2004).
Baumann et al., "PECAM-1 is expressed on hematopoietic stem cells throughout ontogeny and identifies a population of erythroid progenitors," Blood, vol. 104, No. 4, pp. 1010-1016 (Aug. 2004).
Bauvois et al., "TGF-$\beta$1-Stimulated Adhesion of Human Mononuclear Phagocytes to Fibronectin and Laminin is Abolished by IFN-$\gamma$: Dependence on $\alpha$5$\beta$1 and $\beta$2 Integrins," Experimental Cell Research, vol. 222, pp. 209-217 (Jan. 1996).
Breems et al., "Frequency Analysis of Human Primitive Haematopoietic Stem Cell Subsets Using a Cobblestone Area Forming Cell Assay," Leukemia, vol. 8, No. 7, pp. 1095-1104 (Jul. 1994).
Bunting et al., "Effects of Retroviral-Mediated MDR1 Expression on Hematopoietic Stem Cell Self-Renewal and Differentiation in Culture$^a$," Ann. N.Y. Acad. Sci., vol. 872, pp. 125-140 (1999).
Camargo et al., "Single Hematopietic Stem Cells Generate Skeletal Muscle Through Myeloid Intermediates," Nat Med, vol. 9, No. 12, pp. 1520-1527 (Dec. 2003).
Camenisch et al., "ANGPTL3 Stimulates Endothelial Cell Adhesion and Migration via Integrin $\alpha_v\beta_3$ and Induces Blood Vessel Formation in Vivo," The Journal of Biological Chemistry, vol. 277, No. 19, pp. 17281-17290 (May 2002).
Cashman et al., "Changes in the Proliferative Activity of Human Hematopoietic Stem Cells in NOD/SCID Mice and Enhancement of their Transplantability after In Vivo Treatment with Cell Cycle Inhibitors," J. Exp. Med., vol. 196, No. 9, pp. 1141-1149 (Nov. 2002).
Chen et al., "The Endoglin $^{Positive}$ Sca-1 $^{Positive}$ Rhodamine $^{Low}$ Phenotype Defines a near-Homogeneous Population of Long-Term Repopulating Hematopoietic Stem Cells," Immunity, vol. 19, pp. 525-533 (Oct. 2003).
Chen et al., "Identification of endoglin as a functional marker that defines long-term repopulating hematopoietic stem cells," Proceedings of the National Academy of Sciences of the United States of America, vol. 99, No. 24, pp. 15468-15473 (Nov. 2002).
Choong et al., "A novel role for proliferin-2 in the ex vivo expansion of hematopoietic stem cells," FEBS Letters, vol. 550, pp. 155-162 (Aug. 2003).
Cipolleschi et al., "The Role of Hypoxia in the Maintenance of Hematopoietic Stem Cells," Blood, vol. 82, No. 7, pp. 2031-2037 (Oct. 1993).
Conklin et al., "Identification of a Mammalian Angiopoietin-Related Protein Expressed Specifically in Liver," Genomics, vol. 62, No. 3, pp. 477-482 (Dec. 1999).

(Continued)

Primary Examiner — Lora E Barnhart Driscoll
(74) Attorney, Agent, or Firm — Fang Xie; Jennifer A. Camacho; Greenberg Traurig, LLP

(57) ABSTRACT

Methods and kits for expanding the number of hematopoietic stem cells are provided. The methods comprise incubating cells in medium comprising isolated IGFBP-2 and an angiopoietin-like protein (Angptl). Expanded HSCs are provided as well as culture media and kits for the expansion of human HSCs in a defined medium. Methods of administering expanded human HSCs to and individual are provided as well as methods of treating an individual by administering certain growth factors and cytokines.

20 Claims, 21 Drawing Sheets

(56) References Cited

OTHER PUBLICATIONS

Craig et al., "Expression of Thy-1 on Human Hematopoietic Progenitor Cells," *J. Exp. Med.*, vol. 177, pp. 1331-1342 (May 1993).
Cwirla et al., "Peptide Agonist of the Thrombopoietin Receptor as Potent as the Natural Cytokine," *Science*, vol. 276, pp. 1696-1699 (Jun. 1997).
Danet et al., "Expansion of human SCID-repopulating cells under hypoxic conditions," *The Journal of Clinical Investigation*, vol. 112, No. 1, pp. 126-135 (Jul. 2003).
Dawczynski et al., "Changes of serum growth factors (IGF-I,-II and IGFBP-2,-3) prior to and after stem cell transplantation in children with acute leukemia," *Bone Marrow Transplantation*, vol. 32, No. 4, pp. 411-415 (Aug. 2003).
de Haan et al., "In Vitro Generation of Long-Term Repopulating Hematopoietic Stem Cells by Fibroblast Growth Factor-1," *Developmental Cell*, vol. 4, pp. 241-251 (Feb. 2003).
Devine et al., "Clinical application of hematopoietic progenitor cell expansion: current status and future prospects," *Bone Marrow Transplantation*, vol. 31, pp. 241-252 (Feb. 2003).
DiFalco et al., "Preparation of a recombinant chimaera of insulin-like growth factor II and interleukin 3 with high proliferative potency for haemopoietic cells," *Biochem Journal*, vol. 326, Pt. 2, pp. 407-413, (Sep. 1997).
Domen et al., "Self-renewal, differentiation or death: regulation and manipulation of hematopoietic stem cell fate," *Molecular Medicine Today*, vol. 5, pp. 201-208 (May 1999).
Fraser et al., "Expansion In vitro of Retrovirally Marked Totipotent Hematopoietic Stem Cells," *Blood*, vol. 76, No. 6, pp. 1071-1076 (Sep. 1990).
Goodell et al., "Isolation and Functional Properties of Murine Hematopoietic Stem Cells that are Replicating In Vivo," *J. Exp. Med.*, vol. 183, pp. 1797-1806 (Apr. 1996).
Gussoni et al., "Dystrophin Expression in the *mdx* Mouse Restored by Stem Cell Transplantation," *Nature*, vol. 401, pp. 390-394 (Sep. 1999).
Henniker, "CD24," *J. Biol Regulators and Homeostatic Agents*, vol. 15, No. 2, pp. 182-184 (Apr.-Jun. 2001).
Hoeflich et al., "Insulin-like Growth Factor-binding Protein 2 in Tumorigenesis: Protector or Promoter?" *Cancer Research*, vol. 61, pp. 8601-8610 (Dec. 2001).
Hogan et al., "Differential long-term and multilineage engraftment potential from subfractions of human CD34+ cord blood cells transplanted into NOD/SCID mice," *PNAS*, vol. 99, No. 1, pp. 413-418 (Jan. 2002).
Huang et al., "In Vitro Effects of Angiopoietins and VEGF on Hematopoietic and Endothelial Cells," *Biochemical and Biophysical Research communications*, vol. 264, No. 1, pp. 133-138 (Oct. 1999).
Huang et al., "Lymphoid and Myeloid Differentiation of Single Human CD34+, HLA-DR+, CD38− Hematopoietic Stem Cells," *Blood*, vol. 83, No. 6, pp. 1515-1526 (Mar. 1994).
Huynh et al., "Insulin-like growth factor-binding protein 2 secreted by a tumorigenic cell line supports ex vivo expansion of mouse hematopoietic stem cells," *Stem Cells* (Miamisburg), vol. 26, No. 6, pp. 1628-1635 (Jun. 2008).
Issaragrisil et al., "Brief Report Transplantation of Cord-Blood Stem Cells into a Patient with Severe Thalassemia," *The New England Journal of Medicine*, vol. 332 No. 6, pp. 367-369 (Feb. 1995).
Kim et al., "Molecular cloning and characterization of a novel angiopoietin family protein, angiopoietin-3," *FEBS Letters*, vol. 443, pp. 353-356 (Jan. 1999).
Kim et al., "Molecular Cloning, Expression, and Characterization of Angiopoietin-Related Protein," *The Journal of Biological Chemistry*, vol. 274, No. 37, pp. 26523-26528 (Sep. 1999).
Koishi et al., "Angptl3 Regulates Lipid Metabolism in Mice," *Nature Genetics*, vol. 30, pp, 151-157 (Feb. 2002).
Kondo et al., "Biology of Hematopoietic Stem Cells and Progenitors: Implications for Clinical Application," *Annu. Rev. Immunol.*, vol. 21, pp. 759-806 (2003).
Krosl et al., "In Vitro Expansion of Hematopoietic Stem Cells by Recombinant TAT-HOXB4 Protein," *Nature Medicine*, vol. 9, No. 11, pp. 1428-1432 (Nov. 2003).
Kumar et al., "Transforming growth factor-β2 enhances differentiation of cardiac myocytes from embryonic stem cells," *Biochemical and Biophysical Research Communications*, vol. 332, No. 1, pp. 135-141 (Jun. 2005).
Kyoizumi et al., "Implantation and Maintenance of Functional Human Bone Marrow in *SCID*-hu Mice," *Blood*, vol. 79, No. 7, pp. 1704-1711 (Apr. 1992).
Li et al., "Stem Cell Factor Enhances the Survival But Not the Self-Renewal of Murine Hematopoietic Long-Term Repopulating Cells," *Blood*, vol. 84, No. 2, pp. 408-414 (Jul. 1994).
Liao et al., "Yin and Yang of Myocardial Transforming Growth Factor-$β_1$: Timing is Everything," *Circulation*, Editorial, pp. 2416-2417 (2005).
Liu et al., "Functional cloning of IGFBP-3 from human microvascular endothelial cells reveals its novel role in promoting proliferation of primitive CD34+CD38− hematopoietic cells in vitro," *Oncology Research*, vol. 13, pp. 359-371 (2003).
Matsunaga et al., "Thrombopoietin Promotes the Survival of Murine Hematopoietic Long-Term Reconstituting Cells: Comparison With the Effects of FLT3/FLK-2 Ligand and Interleukin-6," *Blood*, vol. 92, No. 2, pp. 452-461 (Jul. 1998).
Miller et al., "Expansion in vitro of adult murine hematopoietic stem cells with transplantable lympho-myeloid reconstituting ability," *Proc. Natl. Acad. Sci. USA*, vol. 94, pp. 13648-13653 (Dec. 1997).
Miyagawa et al., "Insulin and insulin-like growth factor I support the proliferation of erythroid progenitor cells in bone marrow through the sharing of receptors," *British Journal of Haematology*, vol. 109, No. 3, pp. 555-562 (Jun. 2000).
Miyagi et al., "FLK1 + cells derived from mouse embryonic stem cells reconstitute hematopoiesis in vivo in SCID mice," *Exper. Hematology*, vol. 30, No. 12, pp. 1444-1453 (Dec. 2002).
Moore et al., "In Vitro Maintenance of Highly Purified, Transplantable Hematopoietic Stem Cells," *Blood*, vol. 89, No. 12, pp. 4337-4347 (Jun. 1997).
Moore et al., "Expression of CD43 on Murine and Human Pluripotent Hematopoietic Stem Cells[1]," *The Journal of Immunology*, vol. 153, No. 11, pp. 4978-4987 (Dec. 1994).
Murray et al., "Enrichment of Human Hematopoietic Stem Cell Activity in the CD34+Thy-1+Lin− Subpopulation from Mobilized Peripheral Blood," *Blood*, vol. 85, No. 2, pp. 368-378 (Jan. 1995).
Needleman et al., "A General Method Applicable to the Search for Similarities in the Amino Acid Sequence of Two Proteins," *J. Mol. Biol.*, vol. 48, No. 3, pp. 443-453 (Mar. 1970).
Oike et al., "Angiopoietin-Related/Angiopoietin-Like Proteins Regulate Angiogenesis," *Int. J. Hematol.*, vol. 80, No. 1, pp. 21-28 (Jul. 2004).
Oomen et al., "Somatostatin is a selective chemoattractant for primitive (CD34+) hematopoietic progenitor cells" *Experimental Hematology*, vol. 30, No. 2, pp. 116-15 (Feb. 2002).
Orschell-Traycoff et al., "Homing and engraftment potential of Sca-1+ in cells− fractionated on the basis of adhesion molecule expression and position in cell cycle," *Blood*, vol. 96, No. 4, pp. 1380-1387 (Aug. 2000).
Osawa et al., "Long-Term Lymphohematopoietic Reconstitution by a Single C34-Low/Negative Hematopoietic Stem Cell," *Science*, vol. 273, No. 5272, pp. 242-245 (Jul. 1996).
Owen, "Marrow Stromal Stem Cells," *J. Cell Science Supp.*, vol. 10, pp. 63-76 (1988).
Peled et al., "Dependence of Human Stem Cell Engraftment and Repopulation of NOD/SCID Mice on CXCR4," *Science*, vol. 283, pp. 845-848 (Feb. 1999).
Pittenger et al., "Mesenchymal Stem Cells of Human Adult Bone Marrow," *Stem Cell Biology*, vol. 40, Chapter 16, pp. 349-373 (2001).
Reya et al., "A role for Wnt signaling in self-renewal of haematopoietic stem cells," *Nature*, 423, pp. 409-414 (May 2003).
Rossi et al., "Effect of Addition of FLT-3 Ligand and Megakaryocyte Growth and Development Factor on Hemopoietic Cells in Serum-Free Conditions," *Stem Cells and Development*, vol. 13, No. 4, pp. 362-371 (Aug. 2004).

(56) References Cited

OTHER PUBLICATIONS

Sato et al., "Reversible Expression of CD34 by Murine Hematopoietic Stem Cells," *Blood*, vol. 94, No. 8, pp. 2548-2554 (Oct. 1999).
Sauvageau et al., "In Vitro and In Vivo Expansion of Hematopoietic Stem Cells," *Oncogene*, vol. 23, No. 43, pp. 7223-7232 (Sep. 2004).
Schwartz et al., "Suppressive Effects of Recombinant Human Monokine Induced by IFN-γ (rHuMig) Chemokine on the Number of Committed and Primitive Hemopoietic Progenitors in Liquid Cultures of CD34$^+$ Human Bone Marrow Cells," *The Journal of Immunology*, vol. 159, No. 2, pp. 895-904 (Jul. 1997).
Shi et al., "Evidence for Circulating Bone Marrow-Derived Endothelial Cells," *Blood*, vol. 92, No. 2, pp. 362-367 (Jul. 1998).
Shizuru et al., "Hematopoietic Stem and Progenitor Cells: Clinical and Preclinical Regeneration of the Hematolymphoid System," *Annu. Rev. Med.*, vol. 56, pp. 509-538 (2005).
Sitnicka et al., "The effect of Thrombopoietin on the Proliferation and Differentiation of Murine Hematopoietic Stem Cells," *Blood*, vol. 87, No. 12, pp. 4998-5005 (Jun. 1996).
Smith et al., "Measurement of Human and Murine Stem Cell Factor (c-*kit* Ligand)," *Current Protocols in Immunology*, Chapter 6, Unit 17, pp. 6.17.1-6.17.11 (May 2001).
Solar et al., "Role of c-mpl in Early Hematopoiesis," *Blood*, vol. 92, No. 1, pp. 4-10 (Jul. 1998).
Sorrentino, "Clinical Strategies for Expansion of Haematopoietic Stem Cells," *Nat Rev Immunol*, vol. 4, pp. 878-888 (Nov. 2004).
Spangrude et al., "Purification and Characterization of Mouse Hematopoietic Stem Cells," *Science*, vol. 241, No. 4861, pp. 58-62 (Jul. 1988).
Srour et al., "Animal Models for Human Hematopoiesis," *J. Hematother*, vol. 1, pp. 143-153 (Summer 1992).
Sutherland et al., "Functional Characterization of Individual Human Hematopoietic Stem Cells Structured at Limiting Dilution on Supportive Marrow Stromal Layers," *Proc. Natl. Acad. Sci. USA*, vol. 87, pp. 3584-3588 (May 1990).
Turley et al., "Transforming Growth Factor β1 Functions in Monocytic Differentiation of Hematopoietic Cells through Autocrine and Paracrine Mechanisms," *Cell Growth & Differentiation*, vol. 7, pp. 1535-1544 (Nov. 1996).
Valenzuela et al., "Angiopoietins 3 and 4: Diverging Gene Counterparts in Mice and Humans," *Proc. Natl. Acad. Sci. USA*, vol. 96, pp. 1904-1909 (Mar. 1999).
Varnum-Finney et al., "Pluripotent, cytokine-dependent, hematopoietic stem cells are immortalized by constitutive Notch 1 signaling," *Nature Medicine*, vol. 6, No. 11, pp. 1278-1281 (Nov. 2000).
Willert et al., "Wnt Proteins are Lipid-Modified and Can Act as Stem Cell Growth Factors," *Nature*, vol. 423. pp. 448-452 (May 2003).
Yagi et al., "Sustained ex vivo expansion of hematopoietic stem cells mediated by thrombopoietin," *Proc. Natl. Acad. Sci. USA*, vol. 96, pp. 8126-8131 (Jul. 1999).
Yin et al., "AC133, a Novel Marker for Human Hematopoietic Stem and Progenitor Cells," *Blood*, vol. 90, No. 12, pp. 5002-5012 (Dec. 1997).
Zanjani et al., "Engraftment and Long-Term Expression of Human Fetal Hemopoietic Stem Cells in Sheep Following Transplantation In Utero," *J. Clin. Invest.*, vol. 89, pp. 1178-1188 (Apr. 1992).
Zeng et al., "Identification of a Novel Human Angiopoietin-Like Gene Expressed Mainly in Heart," *J Hum Genet*, vol. 48, No. 3, pp. 159-162 (2003).
Zhang et al., "Angiopoietin-like 5 and IGFBP2 stimulate ex vivo expansion of human cord blood hematopoietic stem cells as assayed by NOD/SCID transplantation," *Blood*, vol. 111, pp. 3415-3423 (Oct. 2008).
Zhang et al., "Angiopoietin-like proteins stimulate ex vivo expansion of hematopoietic stem cells," *Nature Medicine*, vol. 12, No. 2, pp. 240-245 (Feb. 2006).
Zhang et al., "Insulin-like growth factor 2 expressed in a novel fetal liver cell population is a growth factor for hematopoietic stem cells," *Blood*, vol. 103, No. 7, pp. 2513-2521 (Apr. 2004).
Zhang et al., "Murine hematopoietic stem cells change their surface phenotype during ex vivo expansion," *Blood*, vol. 105, No. 11, pp. 4314-4320 (Jun. 2005).
Zhang et al., "Prion protein is expressed on long-term repopulating hematopoietic stem cells and is important for their self renewal," *PNAS*, vol. 103, No. 7, pp. 214-2189 (Feb. 2006).
International Search Report for PCT/US2006/020078 dated Apr. 12, 2006.
International Search Report for PCT/US2005/037960 dated Jun. 28, 2006.
International Search Report for PCT/US2008/062365 dated Jan. 20, 2009.
Office Action in U.S. Appl. No. 11/438,847 (now U.S. Patent No. 7,807,464) mailed Nov. 25, 2008.
Office Action in U.S. Appl. No. 11/438,847 (now U.S. Patent No. 7,807,464) mailed Jul. 16, 2009.
Office Action in U.S. Appl. No. 11/255,191 (now U.S. Patent No. 7,767,453) mailed Jul. 16, 2009.
Schwartz, et al., "Suppressive Effects of Recombinant Human Monokine Induced by IFN-γ (rHuMig) Chemokine on the Number of Committed and Primitive Hemopoietic Progenitors in Liquid Cultures of CD34$^+$ Human Bone Marrow Cells", The Journal of Immunology, vol. 159, pp. 895-904, (1997).
Currently pending claims in co-pending U.S. Appl. No. 12/830,709, filed Jul. 6, 2010.
Currently pending claims in co-pending U.S. Appl. No. 12/853,677, filed Aug. 10, 2010.
Notice of Allowance in co-pending U.S. Appl. No. 12/853,677, mailed Apr. 15, 2013.
Final Office Action in co-pending U.S. Appl. No. 12/830,709, mailed Apr. 30, 2013.

\* cited by examiner

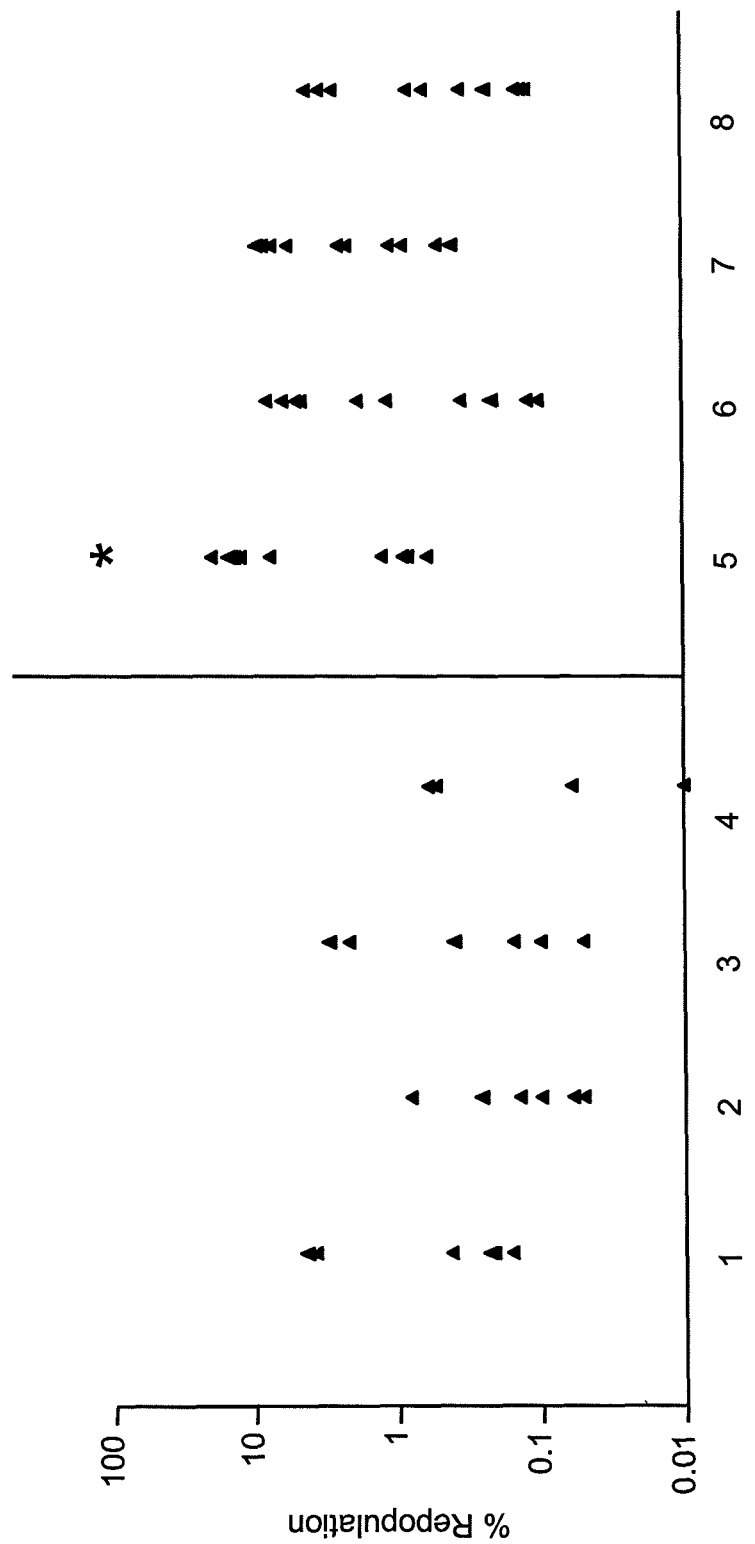

FIG. 8

SEQ ID NO: 3
```
  1 mktftwtlgv lffllvdtgh crggqfkikk inqrryprat dgkeeakkca ytflvpeqri
 61 tgpicvntkg qdastikdmi trmdlenlkd vlsrqkreid vlqlvvdvdg nivnevkllr
121 kesrnmnsrv tqlymqllhe iirkrdnsle lsqlenkiln vttemlkmat ryrelevkya
181 sltdlvnnqs vmitlleeqc lrifsrqdth vspplvqvvp qhipnsqqyt pgllggneiq
241 rdpgyprdlm pppdlatspt kspfkippvt finegpfkdc qqakeaghsv sgiymikpen
301 sngpmqlwce nsldpggwtv iqkrtdgsvn ffrnwenykk gfgnidgeyw lgleniymls
361 nqdnykllie ledwsdkkvy aeyssfrlep esefyrlrlg tyqgnagdsm mwhngkqftt
421 ldrdkdmyag ncahfhkggw wynacahsnl ngvwyrgghy rskhqdgifw aeyrggsysl
481 ravqmmikpi d
```

SEQ ID NO: 4
```
  1 mrplcvtcww lgllaamgav agqedgfegt eegsprefiy lnrykrages qdkctytfiv
 61 pqqrvtgaic vnskepevll enrvhkqele llnnellkqk rqietlqqlv evdggivsev
121 kllrkesrnm nsrvtqlymq llheiirkrd nalelsqlen rilnqtadml qlaskykdle
181 hkyghlatla hnqseiiaql eehcqrvpsa rpvpqpppaa pprvyqppty nriinqistn
241 eiqsdqnlkv lppplptmpt ltslpsstdk psgpwrdclq aledghdtss iylvkpentn
301 rlmqvwcdqr hdpggwtviq rrldgsvnff rnwetykqgf gnidgeywlg leniywltnq
361 gnykllvtme dwsgrkvfae yasfrlepes eyyklrlgry hgnagdsftw hngkqfttld
421 rdhdvytgnc ahyqkggwwy nacahsnlng vwyrgghyrs ryqdgvywae frggsyslkk
481 vvmmirpnpn tfh
```

SEQ ID NO: 5
```
  1 mftiklllfi vplvissrid qdnssfdsls pepksrfaml ddvkilangl lqlghglkdf
 61 vhktkgqind ifqklnifdq sfydlslqts eikeeekelr rttyklqvkn eevknmslel
121 nsklesllee killqqkvky leeqltnliq nqpetpehpe vtslktfvek qdnsikdllq
181 tvedqykqln qqhsqikeie nqlrrtsiqe pteislsskp raprttpflq lneirnvkhd
241 gipaecttiy nrgehtsgmy airpsnsqvf hvycdvisgs pwtliqhrid gsqnfnetwe
301 nykygfgrld gefwlgleki ysivkqsnyv lrieledwkd nkhyieysfy lgnhetnytl
361 hlvaitgnvp naipenkdlv fstwdhkakg hfncpegysg gwwwhdecge nnlngkynkp
421 rakskperrr glswksqngr lysikstkml ihptdsesfe
```

SEQ ID NO: 6
```
  1 msgaptagaa lmlcaatavl lsaqggpvqs ksprfaswde mnvlahgllq lgqglrehae
 61 rtrsqlsale rrlsacgsac ggtegstdlp lapesrvdpe vlhslqtqlk aqnsriqqlf
121 hkvaqqqrhl ekqhlriqhl qsqfglldhk hldhevakpa rrkrlpemaq pvdpahnvsr
181 lhrlprdcqe lfqvgerqsg lfeiqpqgsp pflvnckmts dggwtviqrr hdgsvdfnrp
241 weaykagfgd phgefwlgle kvhsitgdrn srlavqlrdw dgnaellqfs vhlggedtay
301 slqltapvag qlgattvpps glsvpfstwd qdhdlrrdkn cakslsggww fgtcshsnln
361 gqyfrsipqq rqklkkgifw ktwrgryypl qattmliqpm aaeaas
```

SEQ ID NO: 7
```
  1 mmspsqasll flnvcificg eavqgncvhh stdssvvniv edgsnakdes ksndtvcked
 61 ceescdvktk itreekhfmc rnlqnsivsy trstkkllrn mmdeqqasld ylsnqvnelm
121 nrvlllttev frkqldpfph rpvqshgldc tdikdtigsv tktpsglyii hpegssypfe
181 vmcdmdyrgg gwtviqkrid giidfqrlwc dyldgfgdll gefwlglkki fyivnqknts
241 fmlyvalese ddtlayasyd nfwledetrf fkmhlgrysg nagdafrglk kednqnampf
301 stsdvdndgc rpaclvngqs vkscshlhnk tgwwfnecgl anlngihhfs gkllatgiqw
361 gtwtknnspv kiksvsmkir rmynpyfk
```

FIG. 9

```
SEQ ID NO: 1
    1 mwqivfftls cdlvlaaayn nfrksmdsig kkqyqvqhgs csytfllpem dncrsssspy
   61 vsnavqrdap leyddsvqrl qvlenimenn tqwlmkleny iqdnmkkemv eiqqnavqnq
  121 tavmieigtn llnqtaeqtr kltdveaqvl nqttrlelql lehslstnkl ekqildqtse
  181 inklqdknsf lekkvlamed khiiqlqsik eekdqlqvlv skqnsiieel ekkivtatvn
  241 nsvlqkqqhd lmetvnnllt mmstsnsakd ptvakeeqis frdcaevfks ghttngiytl
  301 tfpnsteeik aycdmeaggg gwtiiqrred gsvdfqrtwk eykvgfgnps geywlgnefv
  361 sqltnqqryv lkihlkdweg neayslyehf ylsseelnyr ihlkgltgta gkissisqpg
  421 ndfstkdgdn dkcickcsqm ltggwwfdac gpsnlngmyy pqrqntnkfn gikwyywkgs
  481 gyslkattmm irpadf SEQ ID NO: 2
    1 mlprvgcpal plppppllpl lplllllga sgggggarae vlfrcppctp erlaacgppr
   61 vappaavaav aggarmpcae lvrepgcgcc svcarlegea cgvytprcgq glrcyphpgs
  121 elplqalvmg egtcekrrda eygaspeqva dngddhsegg lvenhvdstm nmlggggsag
  181 rkplksgmke lavfrekvte qhrqmgkggk hhlgleepkk lrpppartpc qqeldqvler
  241 istmrlpder gplehlyslh ipncdkhgly nlkqckmsln gqrgecwcvn pntgkliqga
  301 ptirgdpech lfyneqqear gvdtqrmq
```

EX VIVO EXPANSION OF HUMAN HEMATOPOIETIC STEM CELLS

GOVERNMENT FUNDING

This technology was made with support from the United States government under grant numbers R01 DK 067356-01, 1 K01 CA 120099-01, and 075/P-IRFT, awarded by the National Institutes of Health, and the United States government has certain rights in the technology.

RELATED APPLICATIONS

This application is a national stage application of International Application No. PCT/US2008/062365 filed May 2, 2008, which claims the benefit of and priority to U.S. Provisional Application No. 60/927,668 entitled "Ex Vivo Expansion of Human Hematopoietic Stem Cells" filed May 4, 2007, now expired and U.S. Provisional Application No. 61/014,006 entitled "Method for Expansion and Analysis of Cultured Hematopoietic Stem Cells" filed Dec. 14, 2007, now expired, the contents of which three applications are herein incorporated by reference in their entirety.

BACKGROUND OF THE TECHNOLOGY

The hematopoietic stem cell (HSC), through proliferation and differentiation, gives rise to all lymphoid, myeloid, and erythroid cells. Pluripotent HSCs are thus the basis of bone marrow transplantation and are considered attractive target cells for hematopoietic gene therapy for many clinical conditions. However, these important clinical applications have been severely hampered by the low numbers of HSCs that can be obtained from an animal, as well as difficulties in culturing HSCs in vitro and expanding HSCs for subsequent administration to a patient.

Culture and propagation of stem cells, such as hematopoietic stem cells, typically requires supplementation with unknown factors that allow the stem cells to survive and multiply in number. The unknown factors can be supplied by co-culturing the stem cells with feeder cells which secrete an undefined panel of factors, or can be supplied by adding undefined serum products to the growth medium. Such supplemented medium contains many unknown factors and therefore is not chemically defined.

The presence of unknown factors is problematic when the stem cells are being prepared for in vivo use, especially in humans. In many instances, the unknown factors are from non-human sources (such as bovine serum products). The non-human components may cause an immune reaction in the recipient, or the undefined components could include undetected pathogenic agents such as prions or viruses that would be detrimental to the recipient of the stem cells. There is a need for methods and compositions that allow the in vitro and/or ex vivo propagation of human HSCs in a chemically defined medium, while maintaining the pluripotency of the propagated cells.

SUMMARY

Provided herein is a defined culture medium for expanding human hematopoietic stem cells. The defined medium includes certain growth factors that synergize with each other to stimulate expansion of human HSCs. Surprisingly, as demonstrated herein, a factor produced by non-transfected 293T cells promotes the in vitro expansion of human HSCs. That factor is shown herein to be insulin-like growth factor binding protein 2 (IGFBP-2). The finding that IGFBP-2 promotes the expansion of human hematopoietic stem cells is unexpected in light of the inhibitory effects that exogenous IGFBP-2 has on cell proliferation in different IGF-dependent cell culture systems. (Hoeflich, et al., Canc. Res. 61:8601-8619 (2001)).

As demonstrated herein, IGFBP-2, in combination with one or more Angptl proteins promotes the expansion of human HSCs in a defined culture medium. In some embodiments, human HSCs are expanded in a defined medium by 250 fold or more.

In some embodiments, the method expanding human HSCs comprises incubating human cells in a defined culture medium. The defined culture medium can comprise IGFBP-2 and an angiopoietin-like protein (Angptl). In some embodiments, the defined culture medium can comprise IGFBP-2, Angptl5, fibroblast growth factor 1 (FGF-1), thrombopoietin (TPO), and stem cell factor (SCF). In some embodiments, the method comprises incubating human cells for five days in a defined culture medium.

In some embodiments, the human cells are primary human cells. In some embodiments, the human cells include at least one cell that is capable of differentiating into one or more blood cell types. In some embodiments, the human cells include at least one hematopoietic stem cell.

In some embodiments, the human cells have been selected for cells that express a surface marker selected from the group consisting of CD133 and CD34 prior to being incubated.

Methods of administering hematopoietic stem cells to an individual are also provided. In some embodiments, the method comprises obtaining cells from the individual or a donor. In some embodiments, at least one of the cells is capable of differentiating into one or more blood cell types. The cells are expanded in vitro as provided herein. In some embodiments, the cells are incubated in a defined culture medium comprising an IGFBP-2 and a growth factor selected from the group consisting of angiopoietin 2 or an Angptl. The incubated cells are then administered into the individual.

Methods of treating a patient comprising administering an IGFBP-2 and an Angptl to the individual are provided.

Hematopoietic stem cells that have been expanded in vitro as described herein are also provided.

Culture media and kits for expanding human hematopoietic stem cells in vitro are also provided. In some embodiments, the kit comprises a defined medium suitable for culturing hematopoietic stem cells, an isolated IGFBP-2, and another growth factor selected from the group consisting of angiopoietin 2 or an Angptl. The growth factors can be supplied as separate components, a cocktail, or can be supplied already in combination with HSC growth medium.

In addition, methods are provided for expanding stem cells in culture, including hematopoietic stem cells, by culturing a population of cells that contains stem cells in a culture medium which contains an effective amount of an angiopoietin, such as angiopoietin 2, under conditions sufficient for expansion of the cells. Isolated hematopoietic stem cells are also provided wherein the isolated hematopoietic cells specifically bind an angiopoietin. Culture media and kits for expanding hematopoietic stem cells in vitro are also provided. The culture media and kits comprise an angiopoietin, such as angiopoietin 2 and instructions for expanding hematopoietic stem cells in vitro.

As a result of the methods and compositions provided herein, human HSCs can be expanded in a defined medium while maintaining pluripotency. The cells can be expanded in vitro for research use, or can be expanded in vitro for subsequent administration to an individual (also referred to herein as ex vivo expansion).

The various embodiments described herein can be complimentary and can be combined or used together in a manner understood by the skilled person in view of the teachings contained herein.

BRIEF DESCRIPTION OF FIGURES

FIG. 6E shows multilineage engraftment in NOD/SCID recipients transplanted with 20,000 uncultured CD133$^+$ cells (left panel, n=8) or cultured progeny from 5,000 initial CD133$^+$ cells at normal $O_2$ (right panel, n=10).

FIG. 8 shows SEQ ID NOs. 3-6, amino acid sequences for exemplary angiopoietin-like proteins.

FIG. 9 shows SEQ ID NO. 1, the amino acid sequence for an exemplary angiopoietin 2 protein and SEQ ID NO. 2, the amino acid sequence for an exemplary IGFBP-2 protein.

DETAILED DESCRIPTION

Figure 1A:
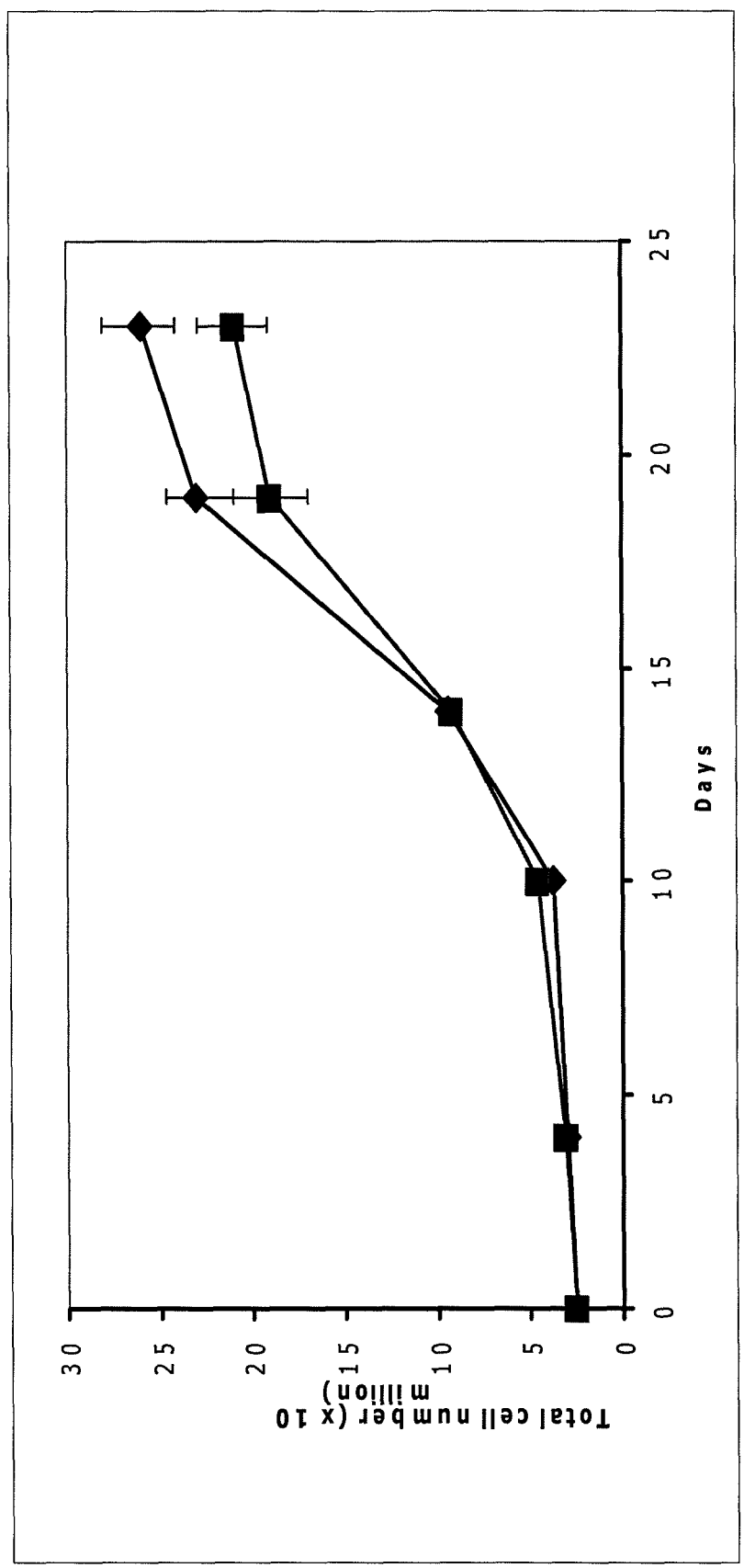
FIG. 1A shows total cell number versus days in culture of total human cord blood cells in the presence of Angptl5 (squares) or Angptl3 (diamonds).

Methods for propagating and/or expanding hematopoietic stem cells (HSCs) are provided, as well as human HSCs produced by the methods. In some embodiments, the human HSCs are expanded in a defined medium. As a result of the methods provided herein, ex vivo expanded human HSCs are available that are free from unknown factors or contaminants typically present in cultured cells.

Culture Medium

As described herein, suitable cells are incubated in a defined (also referred to herein as chemically defined) medium. Defined or chemically defined medium refers to a nutritive medium for culturing cells where every component and quantity thereof present in the medium is known. In some embodiments, the medium is a liquid. In other embodiments, the medium can be a solid such as a tablet or a powder or semisolid material such as a gel. In still other embodiments, the medium can be a liquid that includes a solid structure such as a mesh, porous bead(s), and the like. The defined medium can comprise a base mixture of components, such as Dulbecco's MEM, IMDM, X-Vivo 15 (Cambrex), RPMI-1640 and StemSpan (Stem Cell Technologies). The base mixture can be supplemented with known quantities of other components such as heparin, serum albumin, insulin, transferrin, and the like, or combinations thereof. In some embodiments, the medium is supplemented with 10 µg/ml heparin. The added components can be derived, for example, from any suitable animal source, including, human, bovine, and murine sources. For example, StemSpan comprises IMDM supplemented with bovine serum albumin, human insulin, and human transferrin. The added components and growth factors can be isolated from a biological source (such as tissue, serum, or conditioned medium) or can be recombinantly produced. Suitable hosts for producing recombinant growth factors or other components include, for example, bacteria, yeast, or cell culture. The cell culture can be, for example, insect cell culture, or mammalian cell culture. The growth factor can be glycosylated. In some embodiments, the growth factor is glycosylated in the same or substantially the same manner as the naturally occurring growth factor. The growth factors or other added components described herein can be from any suitable animal, including, for example, mouse, non-human primate, and human.

An "isolated" or "purified" component or growth factor is substantially free of other materials with which it is associated with when produced (e.g., as produced by the biological source or by recombinant methods such as expression in transfected cells). In some embodiments, isolated means less than 0.1%, less than 0.01%, or less than 0.001% of the other materials with which the component or growth factor is associated with when produced is present. In another embodiment, the defined medium is serum free.

The exemplary sequences of growth factors having the GenBank Accession Nos. provided herein are hereby incorporated by reference.

IGFBP-2

In some embodiments, the defined medium includes isolated insulin-like growth factor binding protein 2 (IGFBP-2). IGF Binding Proteins (IGFBPs) are a family of circulating proteins that bind IGF-1 and IGF-2 with an affinity equal or greater than that of the IGF receptors. IGFBP-2 is also known to have inhibitory effects on cell proliferation in different IGF-dependent cell culture systems. (Hoeflich, et al., Canc. Res. 61:8601-8619 (2001)). Surprisingly, as demonstrated herein, IGFBP-2 has a positive effect on the in vitro expansion of human HSCs.

An exemplary IGFBP-2 protein sequence is provided, for example, in GenBank as Accession Number AAA36048 (human insulin-like growth factor binding protein 2; SEQ ID NO: 2, FIG. 9). In addition to IGFBP-2, the skilled artisan will further appreciate that suitable IGFBP-2 includes those proteins and/or polypeptides that have changes in the naturally occurring amino acid sequence wherein the altered sequence retains at least some functional ability of native IGFBP-2. Suitable alterations include changes to or elimination of non-essential amino acid residues as well as conservative amino acid changes (e.g., replacing an amino acid residue with an amino acid residue having a similar side chain).

Suitable IGFBP-2 shares at least 60% sequence identity with SEQ ID NO. 9. In other embodiments, suitable IGFBP-2 shares at least 70% or at least 80% or at least 90%, or at least 95%, or at least 96, 97, 98, or 99% sequence identity with SEQ ID NO. 9 or a biologically active portion thereof.

Suitable analogs of IGFBP-2 include fragments retaining the desired activity and related molecules. Molecules capable of binding the corresponding receptor of IGFBP-2 and initiating one or more biological actions associated with binding to the IGFBP-2 receptor are also within the scope of the technology (e.g., methods, HCSs, media, and kits) provided herein.

Angiopoietin-Like Proteins

The one or more angiopoietin-like protein (Angptl) can be any member of a family of secreted glycosylated proteins that are similar in structure to angiopoietins (Oike et al., Int. J. Hematol. 80:21-8 (2004)). Angptl proteins contain an N-terminal coiled-coil domain and a C-terminal fibrinogen-like domain. Unlike angiopoietins, Angptl proteins do not bind to the tyrosine kinase receptor Tie2. Angptl proteins include Angptl 1, 2, 3, 4, 5, 6, and 7. Angptl proteins also include microfibrillar-associated glycoprotein 4 (Mfap4), and analogs and equivalents thereof. Angptl2 has been described by Kim, I. et al. J Biol Chem 274, 26523-8 (1999)). In addition, Angptl proteins are available commercially (R&D Systems, Abnova Corp). In one embodiment, the Angptl is Angptl 3. In another embodiment, the Angptl is Angptl 5.

Exemplary Angptl proteins are provided, for example in GenBank as Accession Number AAH12368 (human Angptl 1: SEQ ID NO 3; human Angptl2 precursor; SEQ ID NO: 4) Accession Number AAH58287 (human Angptl3 precursor; SEQ ID NO: 5) Accession Number AAH23647 (human Angptl4; SEQ ID NO: 6) and Accession Number AAH49170 (human Angptl5; SEQ ID NO: 7). SEQ ID NOs: 3 through 7 are shown in FIG. 8. Other suitable Angptl proteins share at least 60% sequence identity with any one of SEQ ID NOs: 3 to 7. In other embodiments, suitable Angptl proteins share at least 70% or at least 80% or at least 90%, or at least 95%, or at least 96, 97, 98, or 99% sequence identity with an exemplary Angptl sequence such as SEQ ID NOs: 3, 4, 5, 6, or 7, or biologically active portions thereof. An exemplary sequence for Angptl7 is found in GenBank Accession No. AAH01881. An exemplary sequence for Mfap4 is found in GenBank Accession No. NP_002395.

In addition to sequences provided above for Angptls, the skilled artisan will further appreciate that suitable Angptls include those proteins and/or polypeptides that have changes in the naturally occurring amino acid sequence wherein the altered sequence retains at least some functional ability of the native Angptl. Suitable alterations include changes to or elimination of non-essential amino acid residues as well as conservative amino acid changes (e.g., replacing an amino acid residue with an amino acid residue having a similar side chain).

Suitable analogs of Angptls include fragments retaining the desired activity and related molecules. For example, a suitable analog of an Angptl is a fragment of the angiopoietin-like protein containing the coiled coil domain. For example, the coiled coil domain of an angiopoietin-like protein. Another analog is the fibrinogen-like domain. Fragments of Angptls such as the coiled-coil domain and the fibrinogen-like domain may be easier to express and to purify compared to full-length protein. Molecules capable of binding the corresponding receptor of the Angptl and initiating one or more biological actions associated with binding to the Angptl receptor are also within the scope of the technology provided herein.

Angiopoietin 2

In some embodiments, the defined medium includes angiopoietin 2. An exemplary angiopoietin 2 protein sequence is provided, for example, in GenBank as Accession Number NP_001138 (human angiopoietin 2; SEQ ID NO: 1, FIG. 9). In addition, the skilled artisan will further appreciate that suitable angiopoietin 2 includes proteins and/or polypeptides that have changes in the naturally occurring amino acid sequence wherein the altered sequence retains at lease some functional ability of native angiopoietin 2. Suitable alterations include changes to or elimination of non-essential amino acid residues as well as conservative amino acid changes (e.g., replacing an amino acid residue with an amino acid residue having a similar side chain).

Suitable angiopoietin 2 shares at least 60% sequence identity with SEQ ID NO. 1. In other embodiments, suitable angiopoietin 2 shares at least 70% or at least 80% or at least 90%, or at least 95%, or at least 96, 97, 98, or 99% sequence identity with SEQ ID NO. 1 or a biologically active portion thereof.

Suitable analogs of angiopoietin 2 include fragments retaining the desired activity and related molecules. Molecules capable of binding the corresponding receptor of angiopoietin 2 and initiating one or more biological actions associated with binding to the angiopoietin 2 receptor are also within the scope of the technology provided herein.

Other Growth Factors

In addition to IGFBP-2, angiopoietin 2, or one or more Angptls, other growth factors or cytokines useful to promote expansion of hematopoietic stem cells in methods of the technology can include one or more of: fibroblast growth factor (FGF), insulin growth factor, thrombopoietin (TPO), and stem cell factor (SCF). Accordingly, in another embodiment, the media includes at least two of FGF, IGF, TPO and SCF or analogs and equivalents thereof. Equivalents thereof include molecules having similar biological activity to these factors (i.e. FGF, TPO, IGF and SCF) as wild-type or recombinantly produced cytokines. Analogs include fragments retaining the desired activity and related molecules. For example, TPO is a ligand of the mp1 receptor, thus molecules capable of binding the mp1 receptor and initiating one or more biological actions associated with TPO binding to mp1 are also within the scope of the technology. An example of a TPO mimetic is found in Cwirla et. al., Science 276:1696 (1997).

Cytokines and growth factors are commercially available from several vendors such as, for example, Amgen (Thousand Oaks, Calif.), R & D Systems (Minneapolis, Minn.) and Immunex (Seattle, Wash.).

As indicated above, the concentrations of cytokines or growth factors range from about 0.1 ng/mL to about 1.0 μg/mL. In another embodiment, from about 1 ng/mL to about 500 ng/mL of the factor is used. In another embodiment, from about 10 ng/ml to 100 ng/ml of the factor is used. Other useful concentrations of the growth factors can be readily determined by one of ordinary skill in the art using the teachings contained herein.

In another embodiment, FGF-1, TPO, and SCF are also included in the medium. In another embodiment the SCF is present at 10 ng/ml, TPO at 20 ng/ml, and FGF-1 at 10 ng/ml. In another embodiment, IGF-2, FGF-1, TPO, and SCF are also included in the medium. Other useful concentrations of the growth factors or cytokines can be readily determined by one of ordinary skill in the art using the teachings contained herein.

As described herein, identity or homology to a given amino acid sequence can be determined as the percentage of identity between two sequences. The homology can be determined using methods known in the art, such as by means of computer programs such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, p. 443-453).

Ex Vivo Cultures of Hematopoietic Stem Cells

Cells

The cell or cells to be cultured can include any cell that is capable of differentiating into one or more blood cell types. Exemplary blood cell types include phagocytic immune cells (e.g., granulocytes), monocytes (e.g., macrophage precursor cells), macrophages, eosiniphils, erythrocytes, platelet forming cells (e.g., megakaryocytes), T lymphocytes, B lymphocytes, and natural killer (NK) cells. Suitable cells include primary cells obtained from an individual or donor. Suitable cells can also be capable of self renewal, that is, capable of propagating or increasing in number and remaining at the same developmental stage as the parent cell.

Suitable cells can be isolated, for example, from any known source of hematopoietic stem cells, including, but not limited to, bone marrow, peripheral blood, mobilized peripheral blood (MPB), fetal liver, and umbilical cord blood. Umbilical cord blood is discussed, for example, in Issaragrishi et al., N. Engl. J. Med. 332:367-369 (1995). Bone marrow cells can be obtained from a source of bone marrow, including but not limited to, ilium (e.g., from the hip bone via the iliac crest), tibia, femora, vertebrate, or other bone cavities. Other sources of stem cells include, but are not limited to, ES cells, embryonic yolk sac, fetal liver, and fetal spleen. Methods for obtaining cells from an individual or donor are well known in the art.

For isolation of bone marrow, an appropriate solution can be used to flush the bone, including, but not limited to, salt solution, optionally supplemented with fetal calf serum (FCS) or other naturally occurring factors, in conjunction with an acceptable buffer. In an embodiment, the buffer is at low concentration, generally from about 5 to about 25 mM. Convenient buffers include, but are not limited to, HEPES, phosphate buffers and lactate buffers. Bone marrow can also be aspirated from the bone in accordance with conventional techniques.

Suitable cells and the hematopoietic cells of the technology can be derived from any animal, where hematopoietic stem cells are present. Suitable animals include human, non-human primate, cow, horse, dog, cat, mouse and the like. In an embodiment, the cells are human cells, in still another embodiment, the cells are murine cells.

Animal models for long-term engrafting potential of candidate human hematopoietic stem cell populations include the non-obese diabetic/severe combined immunodeficiency mouse (NOD/SCID) model, the SCID-hu bone model (Kyoizumi et al. (1992) Blood 79:1704; Murray et al. (1995) Blood 85(2) 368-378) and the in utero sheep model (Zanjani et al. (1992) J. Clin. Invest. 89:1179). For a review of animal models of human hematopoiesis, see Srour et al. (1992) J. Hematother. 1:143-153 and the references cited therein. An in vitro model for stem cells is the long-term culture-initiating cell (LTCIC) assay, based on a limiting dilution analysis of the number of clonogenic cells produced in a stromal co-culture after 5 to 8 weeks (Sutherland et al. (1990) Proc. Nat'l Acad. Sci. 87:3584-3588). The LTCIC assay has been shown to correlate with another commonly used stem cell assay, the cobblestone area forming cell (CAFC) assay, and with long-term engrafting potential in vivo (Breems et al. (1994) Leukemia 8:1095).

As used herein, expansion or propagation includes any increase in cell number. Expansion includes, for example, an increase in the number of hematopoietic stem cells over the number of HSCs present in the cell population used to initiate the culture. The methods provided herein provide for the increased survival of existing cells, such as hematopoietic stem cells. The term survival refers to the ability to continue to remain alive or function.

The methods provided herein can be used to stimulate the expansion of any stem cells which expand in the presence of angiopoietin 2, and/or an angiopoietin-like protein and/or IGFBPs, including other types of adult stem cells such as endothelial progenitor cells (Shi, Q. et al. (1998), Blood. 92, 362-367), bone marrow stromal stem cells (Owen, M. (1988), J. Cell Science Supp. 10, 63-76), mesenchymal stem cells (Pittenger, M. F. and Marshak, D. R. (2001), Marshak, D. R., Gardner, D. K., and Gottlieb, D. eds. Cold Spring Harbor, N.Y.: Cold Spring Harbor Laboratory Press 349-374), and skeletal muscle stem cells (Gussoni, E., et al. (1999), Nature. 401, 390-394), embryonic stem cells, as well as others. In another embodiment, the stem cells are endothelial progenitor cells, which are believed to share the same precursor—hemangioblasts—as HSCs.

Subpopulations of cells can also be used in the methods provided herein. For example, a purified "side population" (SP) cells obtained from bone marrow or other sources can be used. Other enriched populations of HSCs can also be used. Methods for isolating enriched populations of HSCs are known to those in the art, e.g. methods for obtaining SP cells are described in Goodell et al., J. Exp. Med. 183, 1797-806 (Apr. 1, 1996).

In addition, a subpopulation of cells enriched for stem cells can be used in the methods described herein. Separation of stem cells from a cell population can be performed by any number of methods, including cell sorting, (e.g., fluorescence activated cell sorting) magnetic beads, and packed columns. The methods typically rely on the presence of certain cell surface markers characteristic of stem cells and/or the absence of certain cell surface markers characteristic of differentiated cells. The methods can also rely on functional assays to measure the engraftment or differentiation potential of the population of cells. Such markers and functional assays are known in the art.

An example of a enriched for stem cells is a population of cells selected for the $CD34^+Thy-1^+LIN^-$ phenotype as described in U.S. Pat. No. 5,061,620. A population of this phenotype typically has an average CAFC frequency of approximately 1/20 (Murray et al. (1995) supra; Lansdorp et al., J. Exp. Med. 177:1331 (1993)). Methods for isolating highly enriched populations of hematopoietic stem cells are further provided in U.S. Pat. No. 5,681,559.

As described herein, hematopoietic stem cells have the ability to differentiate into any of several types of blood cells, including red blood cells, white blood cells, including lymphoid cells and myeloid cells. As described herein, HSCs include hematopoietic cells having long-term engrafting potential in vivo. Long term engrafting potential (e.g., long term hematopoietic stem cells) can be determined using animal models or in vitro models.

The cells can be enriched for stem cells or immature cells, e.g. in a blood cell lineage, prior to culturing according to the methods provided herein. Cells populations highly enriched in stem cells and methods for obtaining them are described in WO 95/05843; WO 95/03693 and WO 95/08105. In a some embodiments, the one or more cells comprise a population of cells that is substantially enriched in hematopoietic stem cells. In other embodiments, the cells cultured according to the methods provided herein are substantially free of stromal cells.

In some embodiments, the cells used in the methods provided herein are selected or enriched for the presence of or absence of particular markers on the surface of the cell. For example, in some embodiments, the cells are selected for the presence of stem cell markers particular for the animal source of the primary tissue. In other embodiments, the cells are selected for the absence of lineage specific markers. In some embodiments, the cells are selected from the presence of particular markers and the absence of other markers. Methods for isolating cells that have particular markers or that do not have particular markers are well known to those skilled in the art.

Regarding lineage specific markers, the absence or low expression of lineage specific markers can be identified by the lack of binding of antibodies specific to the lineage specific markers. The cells or source of cells for use in the methods provided herein can be subjected to negative selection techniques to remove those cells that express lineage specific markers and retain those cells which are lineage negative ("$Lin^-$"). $Lin^-$ generally refers to cells which lack markers such as those associated with T cells (such as CD2, 3, 4 and 8), B cells (such as B220, CD48, CD10, 19 and 20), myeloid cells (such as Mac-1, Gr-1, CD14, 15, 16 and 33), natural killer ("NK") cells (such as CD244, CD2, 16 and 56), RBC (such as Ter119, and glycophorin A), megakaryocytes (CD41), mast cells, eosinophils or basophils. Methods of negative selection are known in the art. Lineage specific markers also include CD38, HLA-DR and CD71.

Various techniques can be employed to separate the cells by initially removing cells of dedicated lineage or having a particular phenotype. Procedures for separation can include, but are not limited to, physical separation, magnetic separation (using antibody-coated magnetic beads), affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique. Techniques providing accurate and rapid separation include, but are not limited to, flow cytometry (e.g., fluorescence activated cell sorting) and cytospin.

The use of physical separation techniques include, but are not limited to, those based on differences in physical (density gradient centrifugation and counter-flow centrifugal elutriation), cell surface (lectin and antibody affinity), and vital staining properties (mitochondria-binding dye rho123 and DNA-binding dye Hoechst 33342). These procedures are well known to those of skill in this art.

The cells obtained either with or without enrichment for hematopoietic stems cells as described above can be used immediately or frozen at liquid nitrogen temperatures and stored. The frozen cells can be thawed and used in the methods described herein.

Cell Culture

In some embodiments of expanding HSC cells, the cells, obtained, for example from a primary tissue source or from a suitable animal, are incubated in a suitable medium. Suitable conditions comprise incubating at 33° to 39° C., and preferably around 37° C. HSCs can be cultured in an oxygen concentration of 1 to 10%. In some embodiments, the HSCs are cultured under hypoxic conditions. In some embodiments, the cells are incubated under normoxic conditions Normoxic conditions can be, for example, 5% $CO_2$ and oxygen at 15% or more. In some embodiments normoxic conditions are 21% $O_2$. Hypoxic conditions can be, for example, 5% $CO_2$ and 5% $O_2$.

Media can be replaced throughout the culture period. In another embodiment, half of the medium is replaced twice per week with fresh media. The cells can be cultured from 3 to 30 days. In another embodiment, the population of cells including HSCs is cultured for at least four weeks. In another embodiment, the population of cells including HSCs is cultured for up to two weeks. In another embodiment, the population of cells including HSCs is cultured for 7 to 14 days. In another embodiment, the population of cells including HSCs is cultured for 10 days.

HSCs can be propagated by culturing or incubating one or more cells in an expansion container and in a volume of a suitable medium. The cells can be cultured such that the culture well contains about 1-100 cells per well. Where the population of cells is bone marrow, the cells can be cultured at a density of about $1\times10^2$ cells to about $1\times10^7$ cells/mL of medium. In another embodiment, the cells can be cultured at a density of about $1\times10^5$ cells to about $1\times10^6$ cells/mL of medium. In another embodiment, the population of cells comprises Side Population (SP) bone marrow cells. The SP bone marrow cells can be cultured at lower density, for example from about $1\times10^2$ to $5\times10^3$ cells/ml. In a separate aspect, the population of cells can be derived from mobilized peripheral blood. The mobilized peripheral blood cells can be cultured at a density of about 20,000 cells/mL to about 50,000 cells/mL; in another embodiment, the mobilized peripheral blood cells is cultured at a density of about 50,000 cells/mL.

Any suitable expansion container, flask, or appropriate tube such as a 12, 24 or 96 well plate, 12.5 $cm^2$ T flask or gas-permeable bag can be used in the methods provided herein. Such culture containers are commercially available from Falcon, Corning or Costar. As used herein, "expansion container" also is intended to include any chamber or container for expanding cells whether or not free standing or incorporated into an expansion apparatus.

Hematopoietic stem cells that have been expanded in vitro as described herein are also provided. It is understood that the descendants of stem cells grown in culture may not be completely identical (either morphologically, genetically, or phenotypically) to the parent cell. However, as provided herein, the descendants of the stem cells possess at least some ability to differentiate into one or more blood cell types as described, supra. Functional characteristics, such as the ability to develop into one or more blood cell types can be measured, for example, using methods and lineage markers as described herein.

Uses for Ex Vivo Expanded Hematopoietic Stem Cells

The expanded cultured hematopoietic stem cells of the technology can be used for a variety of applications, including transplantation, drug discovery, gene cloning, gene delivery, and, gene expression.

Transplantation

The hematopoietic stem cells provided herein can be administered to a subject or an individual. In some embodiments, the hematopoietic stem cells produced by the methods provided herein are used in cell-based therapies, such a bone marrow transplantation. Suitable subject or individuals include any animal as described above. The subject or individual can be any animal suitable for studying hematopoiesis or cell-based therapies in vivo. vertebrate. The subject or individual can be any animal in need of cell-based therapy. In some embodiments, the individual is a mammal. Mammals include, but are not limited to, humans, non-human primates, mice, cows, horses, dogs, cats and the like. In a preferred embodiment, the mammal is a human.

The transplanted stem cells can be autologous (derived from the individual being treated), allogenic (derived from a donor of the same species), or obtained from a histocompatibly matched donor. In some embodiments, the transplanted stem cells can be xenogenic (derived from a animal of a different species from the recipient). Human autologous and allogeneic bone marrow transplantations are currently used as therapies for diseases such as leukemia, lymphoma, and other life-threatening diseases.

With respect to administering the expanded cells provided herein to a patient, an effective amount of expanded cells may range from as few as several hundred or fewer to as many as several million or more. It will be appreciated that the number of expanded cells to be administered will vary depending on the specifics of the disorder to be treated, including but not limited to size or total volume to be treated, as well as the needs and condition of the recipient, among other factors familiar to the medical professional. In some embodiments, between $10^3$ and $10^{10}$ cells per 100 kg person are administered or transplanted into the subject or individual. Methods of administering or transplanting are well known in the art and include, for example, infusion. Expanded cells provided herein can be administered, for example, by intravenous infusion.

In some embodiments, a single administration of cells is provided. In other embodiments, multiple administrations are used. Multiple administrations can be provided over periodic time periods such as an initial treatment regime of 3 to 7 consecutive days, and then repeated at other times.

The expanded cells can be used for reconstituting the full range of hematopoietic cells in an individual following therapies such as, but not limited to, radiation treatment and chemotherapy. Such therapies destroy hematopoietic cells either intentionally or as a side-effect of bone marrow transplantation or the treatment of lymphomas, leukemias and other neoplastic conditions, e.g., breast cancer.

Expanded cells provided herein are also useful as a source of cells for specific hematopoietic lineages. The maturation, proliferation and differentiation of expanded hematopoietic cells into one or more selected lineages may be effected through culturing the cells with appropriate factors including, but not limited to, erythropoietin (EPO), colony stimulating factors, e.g., GM-CSF, G-CSF, or M-CSF, SCF, Flt-3 ligand, interleukins, e.g., IL-1, -2, -3, -4, -5, -6, -7, -8, -13, etc., or with stromal cells or other cells which secrete factors responsible for stem cell regeneration, commitment, and differentiation.

Drug Discovery

Hematopoietic stem cells provided by the methods described herein are useful for drug discovery. For example, culture conditions or growth factors that promote or inhibit such biological responses of stem cells can be identified by exposing the cells to the conditions or factors to be tested. In this way one may also identify, for example, receptors for these factors or agents that interfere with the biological activity of the factor.

The hematopoietic stem cells produced by the methods provided herein can be used in assays for differentiating stem cells into various hematopoietic lineages. These assays may be readily adapted in order to identify substances such as factors which, for example, promote or inhibit stem cell self-regeneration, commitment, or differentiation.

Gene Cloning Strategies

The hematopoietic cells provided herein can be used to identify and clone genes whose expression is associated with proliferation, commitment, differentiation, and maturation of stem cells or other hematopoietic cells, e.g., by subtractive hybridization or by expression cloning using monoclonal antibodies specific for target antigens associated with these biological events or characteristic of a hematopoietic cell type.

Gene Delivery and Expression

Hematopoietic stem cells are also important targets for gene delivery and expression in a subject. Accordingly the hematopoietic cells provided herein can be genetically altered prior to reintroducing the cells into an individual. For example a gene whose expression is expected to have a therapeutic effect on the individual can be introduced into one more of the hematopoietic cells provided herein. The cells can be genetically altered before or after being cultured and/or expanded as described herein. Methods for introducing genes into the cultured cells are well known in the art.

In some aspects of the technology, individuals can be treated by supplementing, augmenting and/or replacing defective and/or damaged cells with cells that express a therapeutic gene. The cells may be derived from cells of a normal matched donor or stem cells from the individual to be treated (i.e., autologous). By introducing normal genes in expressible form, individuals suffering from such a deficiency can be provided the means to compensate for genetic defects and eliminate, alleviate or reduce some or all of the symptoms.

Expression vectors may be introduced into and expressed in autologous or allogeneic expanded hematopoietic cells, or the genome of cells may be modified by homologous or non-homologous recombination by methods known in the art. In this way, one may correct genetic defects in an individual or provide genetic capabilities naturally lacking in stem cells. For example, diseases including, but not limited to, β-thalassemia, sickle cell anemia, adenosine deaminase deficiency, recombinase deficiency, and recombinase regulatory gene deficiency may be corrected in this fashion. Diseases not associated with hematopoietic cells may also be treated, e.g., diseases related to the lack of secreted proteins including, but not limited to hormones, enzymes, and growth factors. Inducible expression of a gene of interest under the control of an appropriate regulatory initiation region will allow production (and secretion) of the protein in a fashion similar to that in the cell which normally produces the protein in nature.

Transduction of Hematopoietic Stem Cell Cultures

The hematopoietic stem cells provided herein can be genetically modified. The introduction of the gene into the hematopoietic stem cell can be by standard techniques, e.g. infection, transfection, transduction or transformation. The HSC cells can be transduced with a therapeutic gene. For example, the transduction can be via a viral vector such as a retroviral vector (e.g. as described in for example, WO 94/29438, WO 97/21824 and WO 97/21825) or a pox viral vector. When transduction is ex vivo, the transduced cells are subsequently administered to the recipient. Thus, the technology provided herein encompasses treatment of diseases amenable to gene transfer into HSCs, by administering the gene ex vivo or in vivo by the methods disclosed herein. For example, diseases including, but not limited to, β-thalassemia, sickle cell anemia, adenosine deaminase deficiency, recombinase deficiency, recombinase regulatory gene deficiency, etc. can be corrected by introduction of a therapeutic gene. Other indications of gene therapy are introduction of drug resistance genes to enable normal stem cells to have an advantage and be subject to selective pressure during chemotherapy. Suitable drug resistance genes include, but are not limited to, the gene encoding the multidrug resistance (MDR) protein.

Examples of modes of gene transfer include e.g., naked DNA, CaPO$_4$ precipitation, DEAE dextran, electroporation, protoplast fusion, lipofection, cell microinjection, and viral vectors, adjuvant-assisted DNA, gene gun, catheters, etc. In another embodiment, a viral vector is used.

One or more polynucleotide of interest can be inserted into a vector using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

Modification of hematopoietic stem cells can comprise the use of an expression cassette created for either constitutive or inducible expression of the introduced transgene. Such an expression cassette can include regulatory elements such as a promoter, an initiation codon, a stop codon, and a polyadenylation signal. Suitable elements that are operable in the stem cells or in cells that arise from the stem cells after infusion into an individual can be used. Moreover, it is necessary that these elements be operably linked to the nucleotide sequence that encodes the protein such that the nucleotide sequence can be expressed in the stem cells and thus the protein can be produced. Initiation codons and stop codons are generally considered to be part of a nucleotide sequence that encodes the protein.

Examples of promoters that may be used to cause expression of the introduced sequence in specific cell types include Granzyme A for expression in T-cells and NK cells, the CD34 promoter for expression in stem and progenitor cells, the CD8 promoter for expression in cytotoxic T-cells, and the CD11b promoter for expression in myeloid cells. In addition, regulatable promoters can be used. Regulatable promoters such as inducible promoters are available commercially.

The exogenous genetic material that includes the transgene operably linked to the regulatory elements may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA, which can integrate into the chromosome, may be introduced into the cell. When introducing DNA into the cell, reagents, which promote DNA integration into chromosomes, may be added. DNA sequences, which are useful to promote integration, may also be included in the DNA molecule. Alternatively, RNA may be introduced into the cell.

Selectable markers can be used to monitor uptake of the desired gene into the hematopoietic stem cells of the technology. These marker genes can be under the control of any promoter or an inducible promoter. These are well known in the art and include genes that change the sensitivity of a cell to a stimulus such as a nutrient, an antibiotic, etc. Genes include those for neo, puro, and tk, multiple drug resistance (MDR), etc. Other genes express proteins that can readily be screened for such as green fluorescent protein (GFP), blue fluorescent protein (BFP), luciferase, and LacZ.

As used herein, therapeutic gene can be an entire gene or only the functionally active fragment of the gene capable of compensating for the deficiency in the patient that arises from the defective endogenous gene. Therapeutic gene also encompasses antisense oligonucleotides or genes useful for antisense suppression and ribozymes for ribozyme-mediated therapy. Therapeutic genes that encode dominant inhibitory oligonucleotides and peptides as well as genes that encode regulatory proteins and oligonucleotides also are encompassed by this technology. Generally, gene therapy will involve the transfer of a single therapeutic gene although more than one gene may be necessary for the treatment of particular diseases. The therapeutic gene can be a normal, e.g., wild-type, copy of the defective gene or a functional homolog. In a separate embodiment, the therapeutic gene is a dominant inhibiting mutant of the wild-type. More than one gene can be administered per vector or alternatively, more than one gene can be delivered using several compatible vectors. Depending on the genetic defect, the therapeutic gene can include the regulatory and untranslated sequences. For gene therapy in human patients, the therapeutic gene will generally be of human origin although genes from other closely related species that exhibit high homology and biologically identical or equivalent function in humans may be used, if the gene product does not induce an adverse immune reaction in the recipient. For example, a primate insulin gene whose gene product is capable of converting glucose to glycogen in humans would be considered a functional equivalent of the human gene. The therapeutic gene suitable for use in treatment will vary with the disease. For example, a suitable therapeutic gene for treating sickle cell anemia is a normal copy of the globin gene. A suitable therapeutic gene for treating SCID is the normal ADA gene.

EXAMPLES

Results

Culture of Total Human Cord Blood Cells in the Presence of Angptl5 or Angptl3 Stimulates Ex Vivo Expansion of Human HSCs.

Total human cord blood cells were cultured in STIF medium containing Angptl3 or Angptl5. (Conklin, D. et al. Genomics 62, 477-82 (1999); Zeng, L. et al. J Hum Genet. 48, 159-62 (2003)).

$2.5 \times 10^7$ total cord blood cells were seeded at a density of $1 \times 10^6$ cells/ml serum-free STIF medium containing 100 ng/ml Angptl3 or Angptl5, and total cell numbers were counted at indicated time. After 23 days of culture, the number of total cells in the presence of Angptl3 increased about 10 fold to $2.6 \pm 0.3 \times 10^8$ (FIG. 1A. diamonds), and the cells cultured with Angptl5 increased to $2.2 \pm 0.3 \times 10^8$ (squares). The cultured cells contained mostly suspension cells with a minor adherent subpopulation.

Figure 1B:
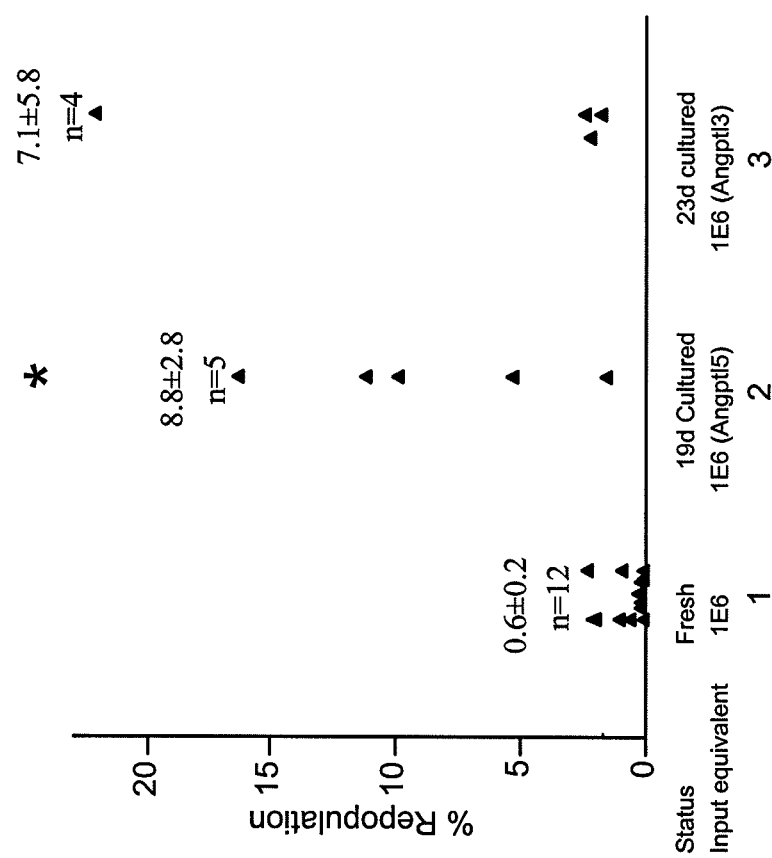
FIG. 1B shows the amount of human chimerism in the bone marrow of NOD/SCID mice transplanted with $1 \times 10^6$ uncultured human mononuclear cord blood cells (col. 1), or the progeny of $1 \times 10^6$ initial human cord blood cells cultured in serum free STIF plus Angptl5 (col. 2) or Angptl3 (col. 3). Each symbol represents the engraftment of a single transplanted mouse assayed at two months post-transplant (n=5-12). (* Significantly different from lane 1 value. Student's t-test, p<0.001.)

NOD/SCID repopulation assays were conducted to test whether ex vivo-expanded cells were capable of engraftment. FIG. 1B shows the amount of human chimerism in the bone marrow of NOD/SCID mice transplanted with $1 \times 10^6$ uncultured human mononuclear cord blood cells, or the cultured progeny of $1 \times 10^6$ initial human cord blood cells. Each symbol represents the engraftment of a single transplanted mouse assayed at two months post-transplant (n=5-12). (* Significantly different from lane 1 value. Student's t-test, p<0.001.) Thus, $1 \times 10^6$ or $3 \times 10^6$ uncultured cells, or the cultured progenies of $1 \times 10^6$ initial cells were injected into sublethally irradiated NOD/SCID recipients. When $9.2 \times 10^6$ cells, cultured with Angptl5 for 19 days (which is the progeny of $1 \times 10^6$ initially plated total cord blood cells), were transplanted, an average human hematopoietic chimerism of 8.8% was observed 2 months after transplantation (FIG. 1B, lane 2). This is much greater than the 0.6% engraftment shown by the equivalent $1 \times 10^6$ uncultured cells (FIG. 1B, lane 1; p<0.001, student's t-test). The cells cultured in the presence of Angptl3 for 23 days also engrafted recipients, with an average chimerism of 7.1% (FIG. 1B, lane 3).

Non-Transfected 293T Cells Stimulates Ex Vivo Expansion of HSCs

Figure 2A:
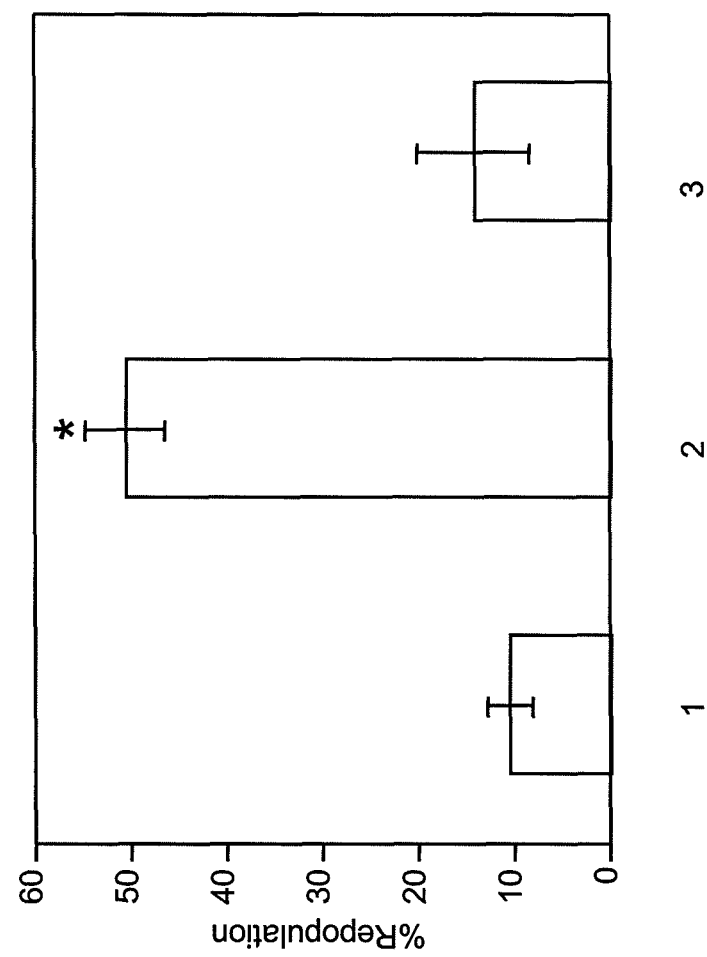
FIG. 2A is a bar graph showing percent repopulation using murine HSCs after culturing in serum-free IMDM supplemented with 10 ng/ml SCF, 20 ng/ml TPO, 20 ng/ml IGF-2, and 10 ng/ml FGF-1, bar 1; freshly collected conditioned medium from 293T cells, bar 2; or in the same conditioned medium after freeze/thaw, bar 3.

Surprisingly, as demonstrated herein, serum-free conditioned medium collected from non-transfected 293T cells stimulates ex vivo expansion of HSCs Twenty freshly isolated CD45.2 bone marrow SP Sca-1+ CD45+ cells were cultured for 10 days in serum-free IMDM supplemented with 10 ng/ml SCF, 20 ng/ml TPO, 20 ng/ml IGF-2, and 10 ng/ml FGF-1 (STIF medium; FIG. 2A, bar 1), in freshly collected serum-free conditioned STIF medium from 293T cells (bar 2), or in the same conditioned medium after freeze/thaw (bar 3). The cultured cells were co-transplanted with $1 \times 10^5$ CD45.1 total bone marrow cells into CD45.1 recipients (n=5-6).

Figure 2B:
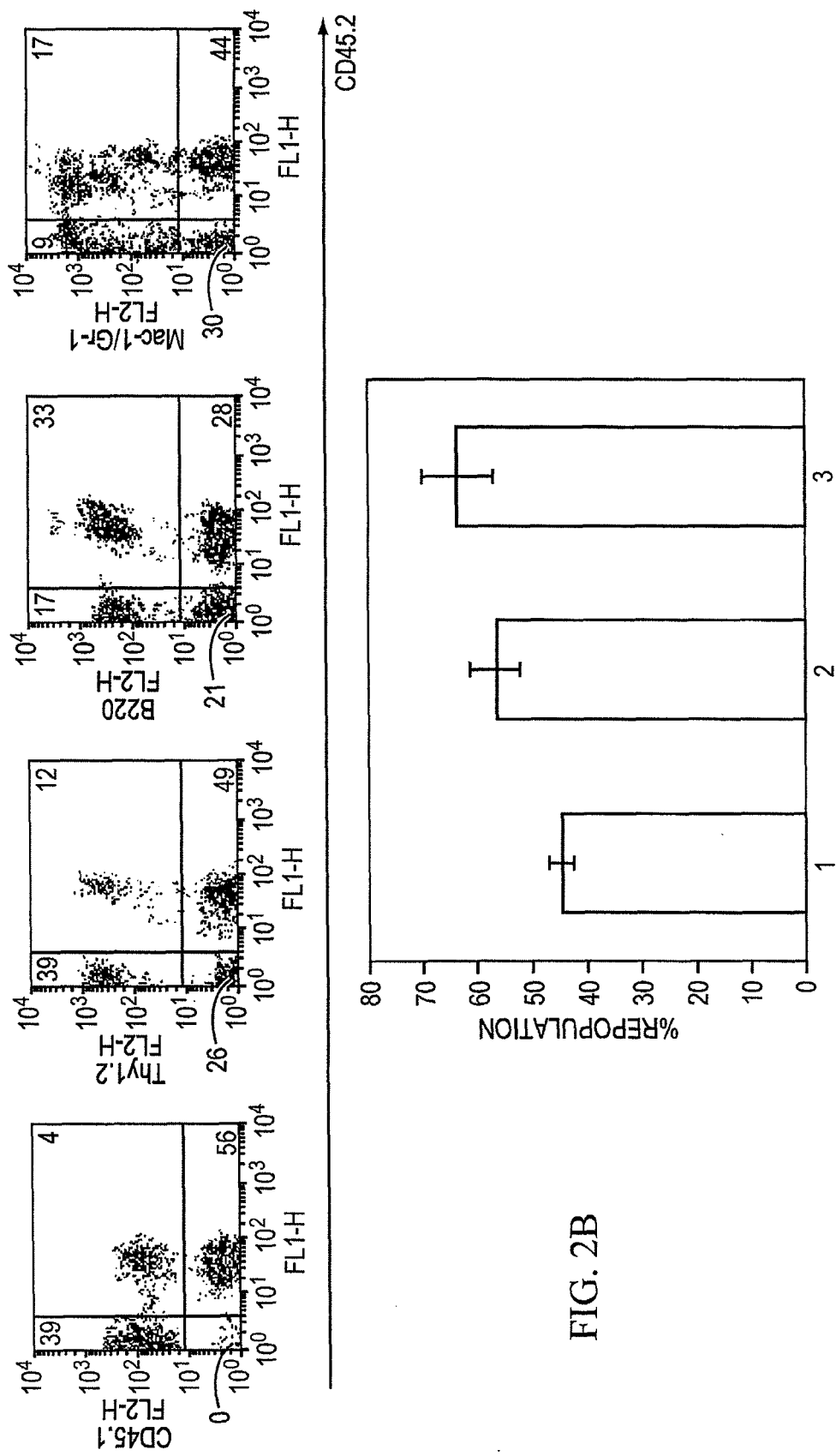
FIG. 2B, top panel shows a representative FACS analysis of the repopulation of myeloid and lymphoid lineages in mice that received cultured cells from conditions represented by bar 2 of FIG. 2A, at 5 months post-transplant and a bar graph; the bottom panel shows a summary of the percent repopulation data from six mice that received cultured cells from conditions represented by bar 2 of FIG. 2A for T-lymphoid (bar 1), B-lymphoid (bar 2), and myeloid (bar 3) cells.

FIG. 2B shows the multilineage contribution of cultured cells at conditions represented by bar 2 of FIG. 2A at 5 months post-transplant (n=6). Data shown in the top panel are representative FACS plots of peripheral blood mononuclear cells from one mouse at 5 months post-transplant (from bar 2 of FIG. 1A). Percentages of cells in each quadrant are listed. The summary of percent repopulation data from mice in bar 2 of FIG. 1A for T-lymphoid, B-lymphoid, and myeloid cells is plotted in the bottom panel.

Serum-free 293T conditioned medium was analyzed by mass spectrometry in order to identify potential candidate proteins that stimulated ex vivo expansion of HSCs. Peptides from several proteins were identified. A partial list of peptides identified in the mass spectrometry analysis of the fraction of serum-free IMDM based conditioned medium of 293T cells that contained proteins smaller than 70 kD is shown in Table I. Proteins found in common with the control serum-free IMDM sample are not shown.

TABLE I

| | Accession No. | | | | |
|---|---|---|---|---|---|
| | P18965 | PO1033 | POCOP6 | P35555 | P36955 |
| Gene | IGFBP-2 | Timp-1 | NPS | Fibrillin-1 | PEDF |
| # peptides | 37 | 20 | 12 | 13 | 15 |
| Total peptides | 46 | 22 | 24 | 22 | 22 |
| % of coverage | 8.45% | 5.32% | 15.01% | 5.70% | 2.99 |
| M.W. | 35114 | 23156 | 10096 | 26129 | 46313 |

Figure 3:
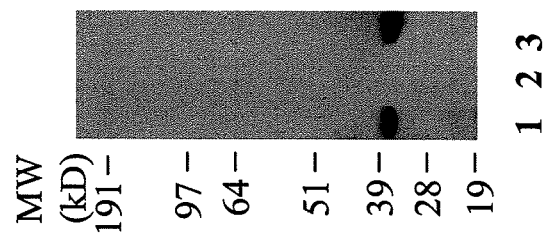
FIG. 3 shows a Western blot of IGFBP-2 (lane 1), serum-free 3T3 conditioned medium (lane 2), and serum-free 293T conditioned medium (lane 3) separated on an SDS PAGE gel and probed with anti-IGFBP-2 antibody.

As demonstrated herein, IGFBP-2 is expressed in serum-free 293T conditioned medium. FIG. 3 shows western blot analysis of purified human IGFBP-2 (positive control; lane 1), serum-free 3T3 conditioned medium (negative control; lane 2), and serum-free 293T conditioned medium (lane 3) detected by anti-human IGFBP-2 polyclonal antibody.

Purified IGFBP-2 Stimulates Ex Vivo Expansion of HSCs.

Figure 4A:
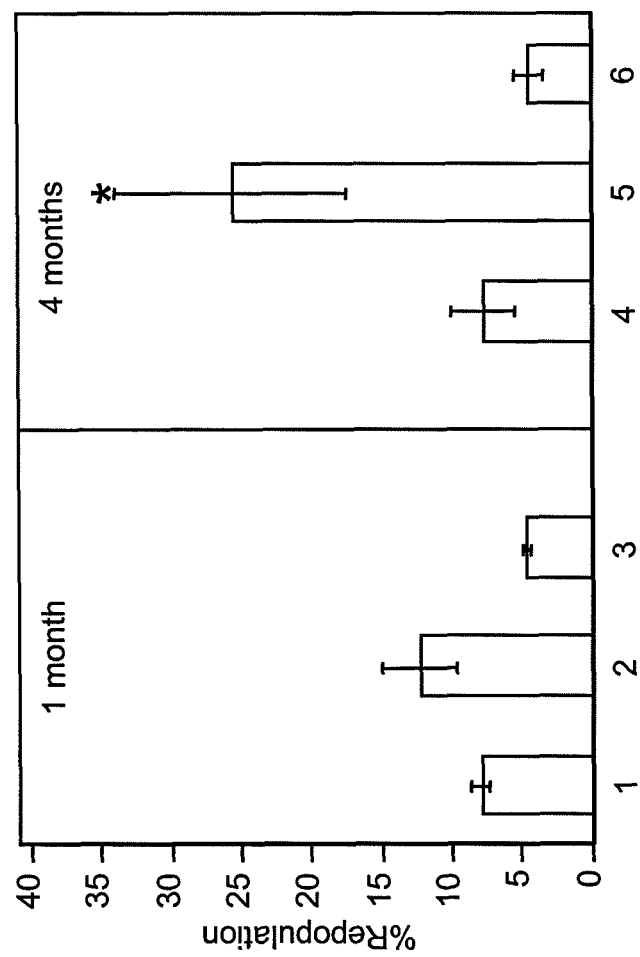
FIG. 4A shows percent repopulation 1 month (left panel) and 4 months (right panel) after engraftment of mice with murine HSCs after culturing in STIF medium plus Angptl3 (col. 1 and 4), STIF medium plus Angptl3 and IGFBP-2 (col. 2 and 5), STIF medium plus Angptl3 and Timp-1 (col. 3 and 6).

As demonstrated herein, IGFBP-2 stimulates ex vivo expansion of HSCs. Twenty CD45.2 bone marrow SP Sca-$1^+$ CD$45^+$ cells were cultured for 5 days in STIF medium with 100 ng/ml Angptl3 (bars 1 and 4); in the same medium with 500 ng/ml IGFBP-2 (bars 2 and 5); and in the same medium with 200 ng/ml Timp-1 (bars 3 and 6) (see FIG. 4A). The cells were then cotransplanted with $1\times10^5$ CD45.1 total bone marrow cells into CD45.1 recipients (n=5). Engraftments at 1 month or 4 months post-transplant are shown in FIG. 4A. (* Significantly different from bars 4 and 6 values. Student's t-test, p<0.05.)

Figure 4B:
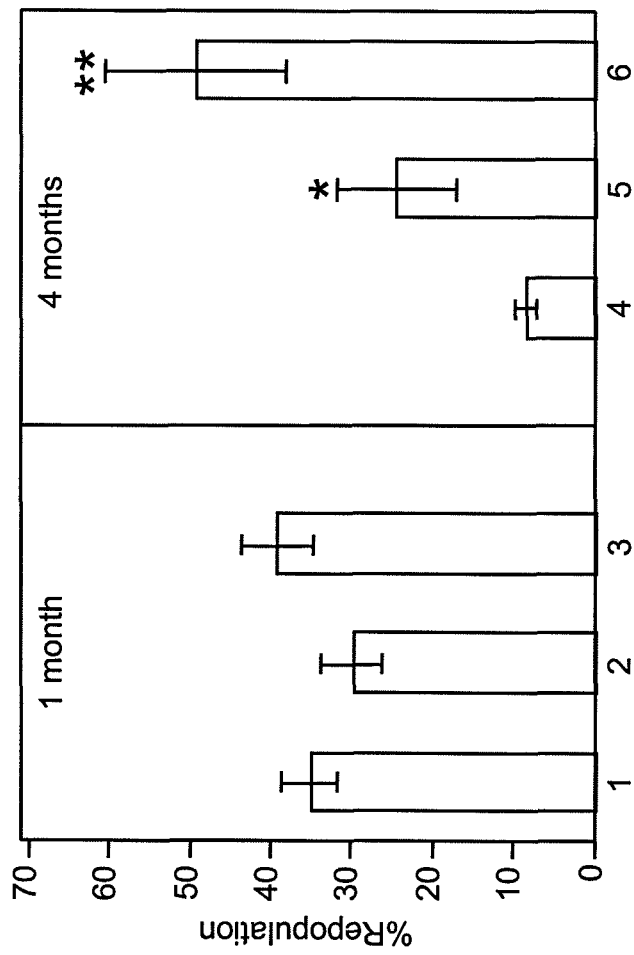
FIG. 4B shows percent repopulation 1 month (left panel) and 4 months (right panel) after engraftment of mice with murine HSCs after culturing in STIF medium plus Angptl3 (col. 1 and 4), STIF medium plus IGFBP-2 (col. 2 and 5), STIF medium plus Angptl3 and IGFBP-2 (col. 3 and 6).

Twenty CD45.2 bone marrow SP Sca-$1^+$CD$45^+$ cells were cultured for 10 days in serum-free medium with 10 ng/ml SCF, 20 ng/ml TPO, 10 ng/ml FGF-1 (STF medium), and 100 ng/ml Angptl3 (bars 1 and 4); in STF medium with 500 ng/ml IGFBP-2 (bars 2 and 5); and in STF medium with 500 ng/ml IGFBP-2 and 100 ng/ml Angptl3 (bars 3 and 6) (see FIG. 4B). The cells were then cotransplanted with $1\times10^5$ CD45.1 total bone marrow cells into CD45.1 recipients (n=6-7). Engraftments at 1 month or 4 months post-transplant are shown in FIG. 4B. (* and ** Significantly different from bar 4 or bar 5 value respectively. Student's t-test, p<0.05.)

Figure 4C:
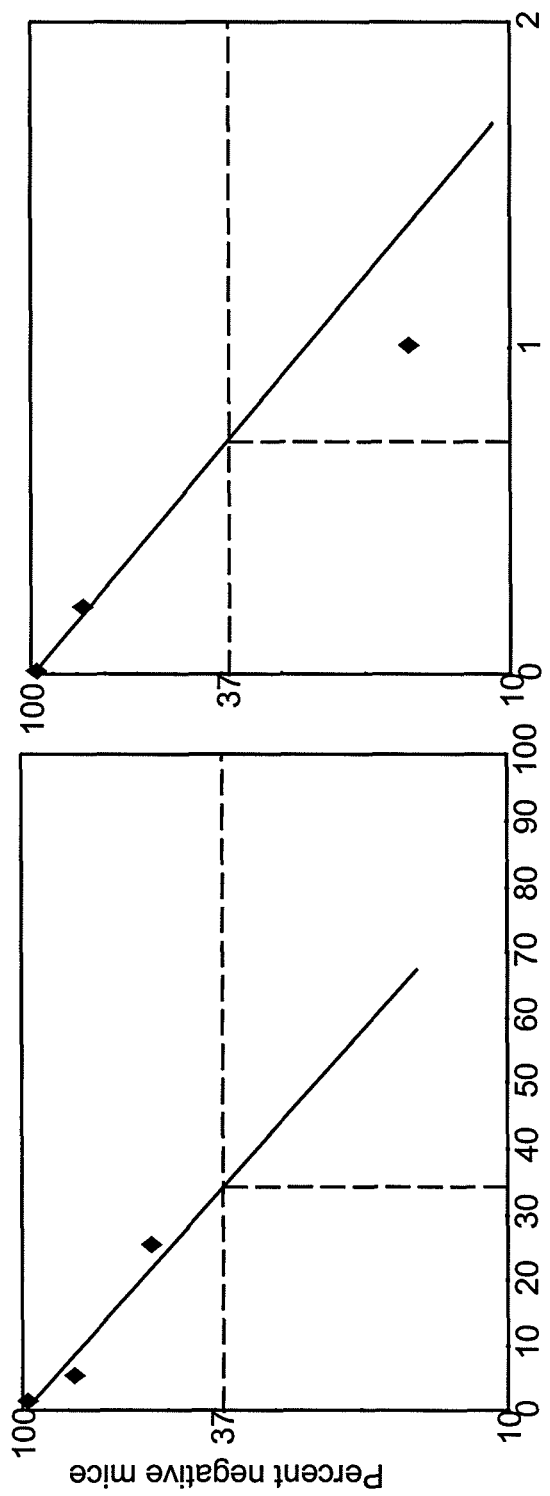
FIG. 4C shows limiting dilution analysis of the repopulating ability of adult BM SP CD45$^+$Sca-1$^+$ cells before culture (left) and after culture for 21 days in conditioned STIF medium containing 100 ng/ml of purified Angptl3 and 500 ng/ml IGFBP-2 (right).

FIG. 4C shows limiting dilution analysis of the repopulating ability of adult BM SP CD$45^+$Sca-$1^+$ cells before culture (left) and after culture for 21 days in serum-free conditioned STF medium containing 100 ng/ml of purified Angptl3 and 500 ng/ml IGFBP-2 (right). Irradiated CD45.1 congenic mice were injected with $1\times10^5$ CD45.1 BM competitor cells and 1, 5, 25, or 100 freshly isolated SP CD$45^+$Sca-$1^+$ cells (left; n=24) or the cultured progenies of 0.2, 1, 4, or 10 SP CD45+ Sca-1+ cells (right; n=26). 100 Freshly isolated SP Sca-1+ CD45+ cells and the cultured progeny of 4 or 10 input cells repopulated all recipients and these data points are not plotted. Plotted is the percentage of recipient mice containing less than 1% CD45.2 populations in nucleated peripheral blood cells 4 months after transplant versus the number of cells injected.

Culture of Human Cord Blood CD$133^+$Cells in the Presence of Angptl5 and IGFBP-2 Stimulates Ex Vivo Expansion of HSCs by Over 250 Fold.

It was surprisingly found that IGFBP-2 can replace IGF-2 in supporting the ex vivo expansion of mouse HSCs. In addition, in the presence of STF medium, IGFBP-2 promoted the ex vivo expansion human cord blood HSCs CD$133^+$ cells by over 250 fold.

Figure 5A:
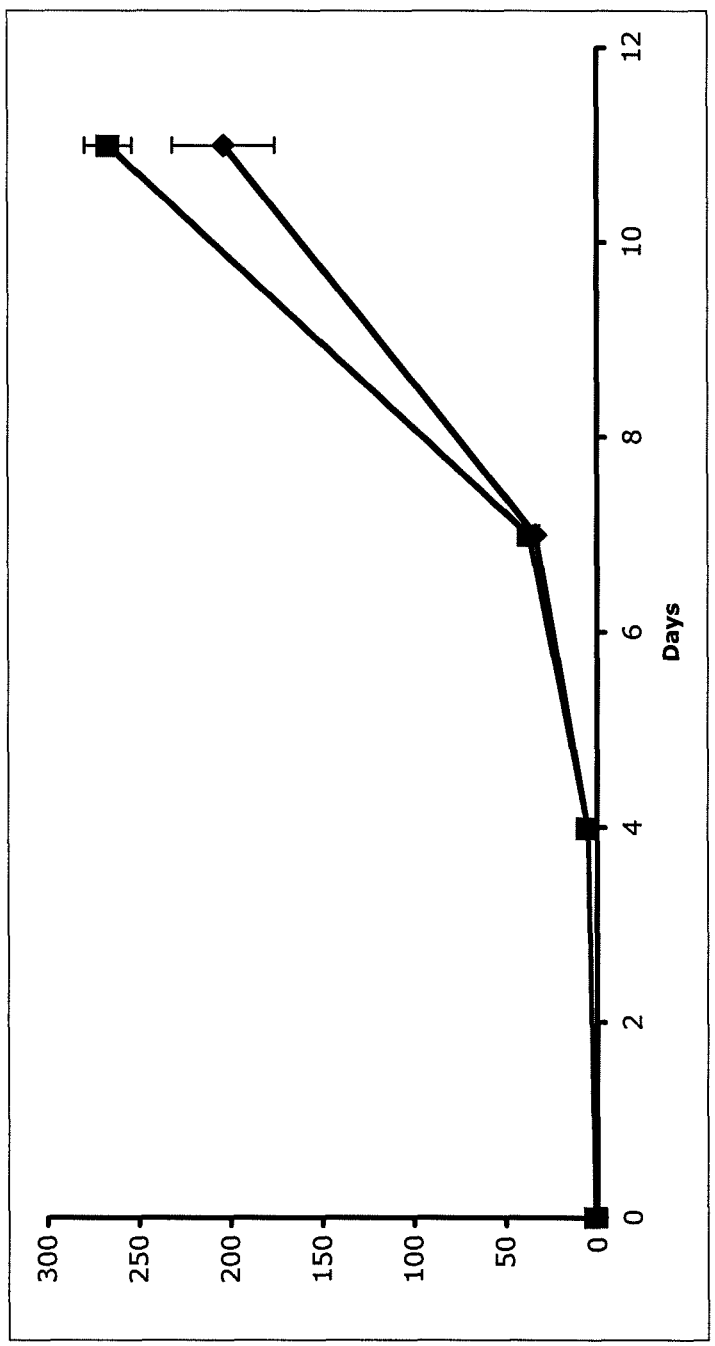
FIG. 5A shows cell number over time in days of human HSCs cultured in STF medium containing Angptl 5 (squares), or cultured in STF medium (diamonds).

Culture of $1\times10^5$ human cord blood CD$133^+$ cells was initiated in serum-free STF medium, or in serum-free STF medium supplemented with 500 ng/ml Angptl5 and 500 ng/ml IGFBP-2 and cultured in a low $O_2$ environment (5% $O_2$). Total cell numbers were counted. As shown in FIG. 5A, the number of total cells increased greater than 200 fold after 11 days of culture either in serum-free STF medium or serum-free STF medium containing Angptl5 and IGFBP-2.

Figure 5B:
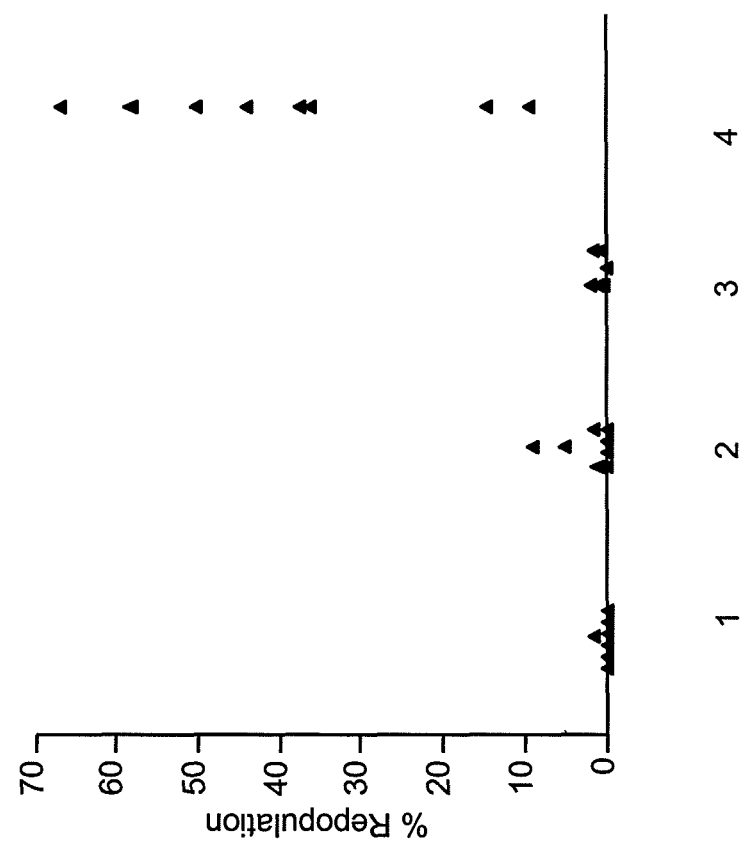
FIG. 5B shows % repopulation by 8000 fresh cells (col. 1), 15000 fresh cells (col. 2), 8000 cells cultured in STF medium (col. 3), or 8000 cells cultured in STF medium containing Angptl5 and IGFBP-2 (col. 4).

IGFBP-2 and Angptl5 Promote Engraftment and Chimerism of Human Cord Blood Cells in a Mouse Model The amount of human chimerism in the bone marrow of NOD/SCID mice transplanted with 8,000 or 15,000 uncultured (fresh) human cord blood CD$133^+$ cells, or the progeny from 8,000 initial CD$133^+$ cells cultured in serum-free STF medium with or without Angptl5 and IGFBP-2 for 11 days was measured. 8,000 uncultured CD$133^+$ cells were capable of engraftment in 1 out of 7 recipients 2 months post-transplant, and the average chimerism was 0.2% (FIG. 5B, lane 1). 15,000 uncultured CD$133^+$ cells showed an increased but still modest engraftment; there was positive engraftment of 4 of 8 mice (average chimerism 2.0% of total cells; FIG. 5B, lane 2).

In striking contrast, $2.1\times10^6$ cells after culture with serum free STF medium with Angptl5 and IGFBP-2, that is, the progeny of 8,000 initial cells after 11 days of culture, engrafted all recipient mice, and showed significantly increased chimerism relative to 8,000 or 15,000 uncultured sells (average 39.5%) (FIG. 5B, lane 4; p<0.05, student's t-test). The cultured progeny of the same number of initial cells (8,000) cultured in STF medium without Angptl5 and IGFBP-2 (now $1.6\times10^6$ cells) only exhibited a poor engraftment, similar to that of their uncultured counterparts (FIG. 5B, lane 3). Thus, Angptl5 and IGFBP-2 support the ex vivo expansion of human SOD-repopulating cells (SRCs) in a defined medium. Each symbol represents the engraftment of a single transplanted mouse assayed at two months post-transplant (n=7-8). (* Significantly different from lanes 1-3 values. Student's t-test, p<0.05.)

Figure 5C:
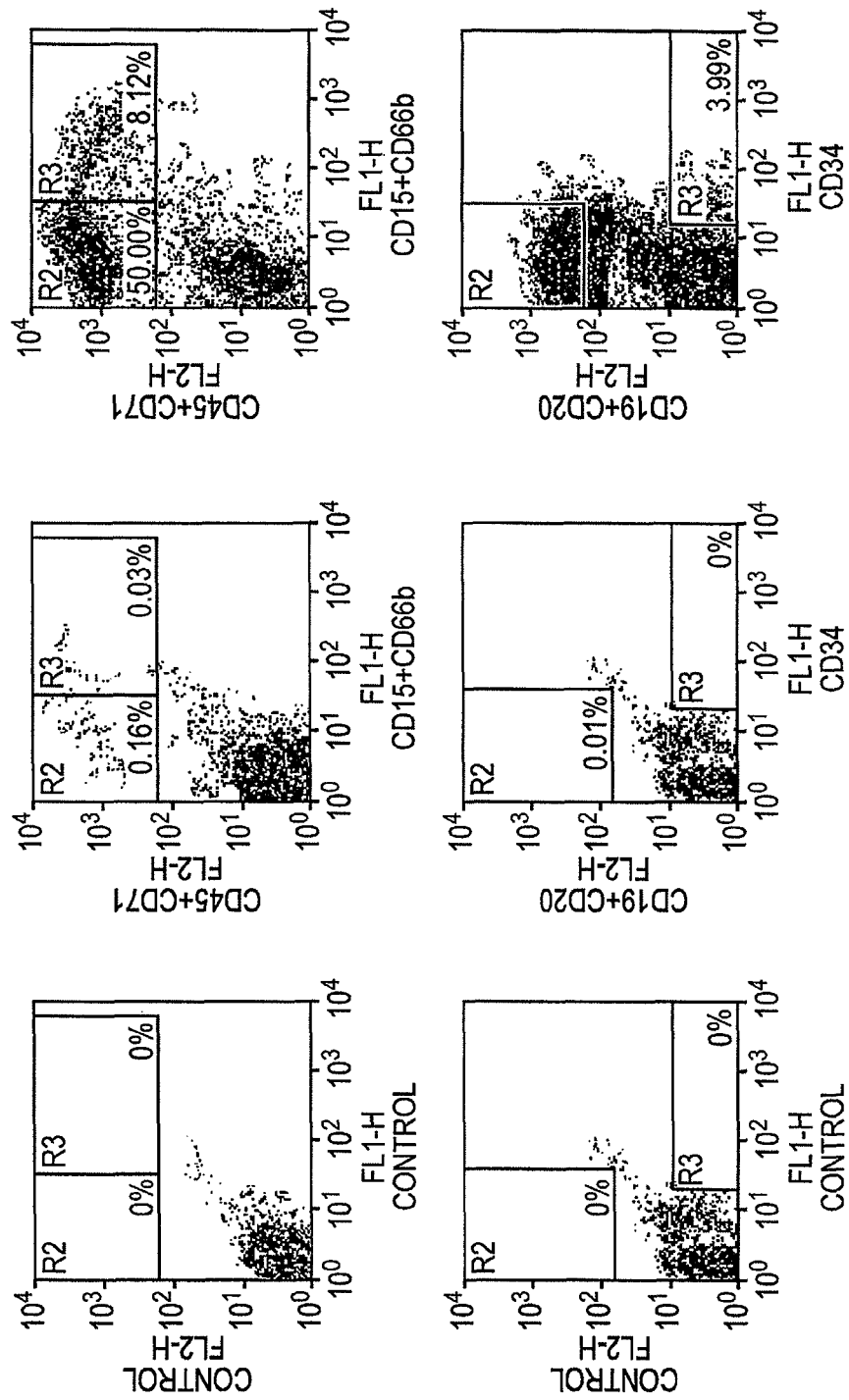
FIG. 5C shows FACS analysis of human hematopoietic engraftment at 2 months in a representative mouse that was transplanted with uncultured (fresh) or cultured human cord blood CD133$^+$ cells.

FIG. 5C shows human hematopoietic engraftment at 2 months in a representative mouse that was transplanted with uncultured (fresh) or cultured human cord blood CD$133^+$ cells. Representative FACS plots of bone marrow cells from one mouse at the condition represented by lane 1 of (FIG. 5B) (Fresh), or at the condition represented by lane 4 of (FIG. 5B) (Cultured), at 2 months post-transplant. Percentages of cells in each quadrant are listed. Transplant with cells cultured in serum-free STF medium containing Angptl5 and IGFBP-2 (lane 4 of FIG. 5B) displayed a much higher engraftment of total hematopoietic (CD45/$71^+$), myeloid (CD15/$66b^+$), B-lymphoid (CD$34^-$CD19/$20^+$), and primitive (CD$34^+$) human cells than the mouse transplanted with uncultured cells (lane 1 of FIG. 5B).

Figure 5D:
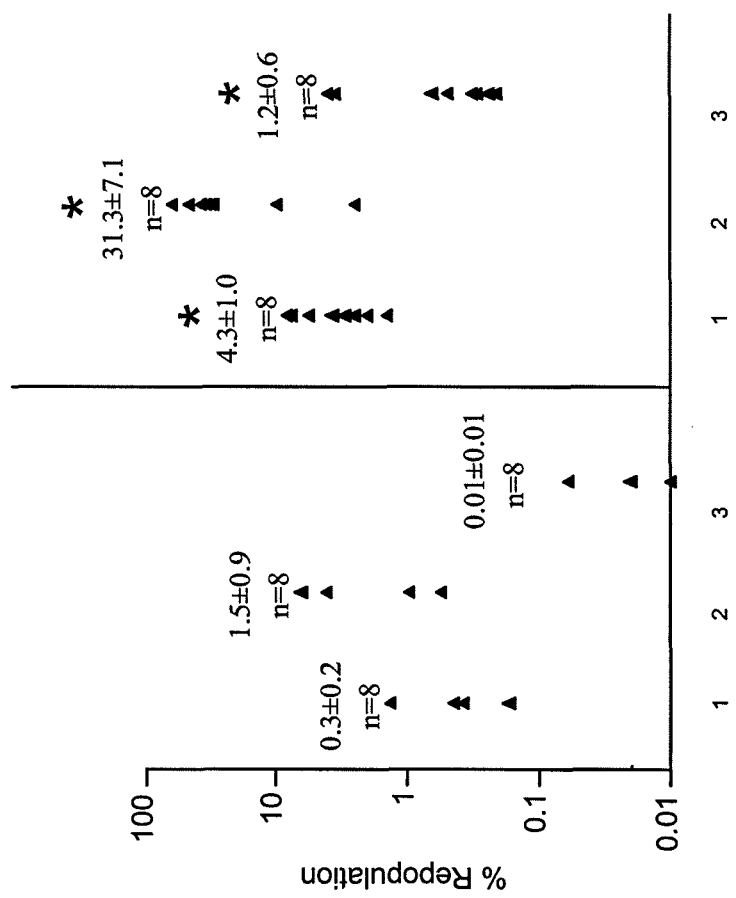
FIG. 5D shows the summary of multilineage engraftment data from mice transplanted with uncultured cells (left panel) and cells cultured in STF medium containing Angptl5 and IGFBP-2 (right panel) showing % repopulation with myeloid (CD15/66b+, cols. 1, 4), B-lymphoid (CD34−CD19/20$^+$, cols. 2, 5), and primitive (CD34$^+$, cols. 3, 6) human cells.

The summary of multi-lineage engraftment of mice transplanted with uncultured cells (FIG. 5B lane 2) and cells cultured in STF medium containing Angptl5 and IGFBP-2 (FIG. 5B lane 4) is shown in FIG. 5D. The progeny of 8,000 cells, after culture, repopulated myeloid and lymphoid lineages 2 months post-transplant, demonstrating the expansion of human stem cell activity. Some mice transplanted with uncultured cells had zero percent donor repopulation and these data points are not plotted. (* Values are significantly different from the values of the uncultured cells. Student's t-test, p<0.05.) FIG. 5D shows human hematopoietic engraftment at 2 months in a representative mouse that was transplanted with uncultured or cultured human cord blood CD$133^+$ cells. The progeny of 8,000 cells, after culture, repopulated myeloid and lymphoid lineages 2 months post-transplant, demonstrating the expansion of human stem cell activity.

Expansion of Human HSCs in Culture

Figure 5E:
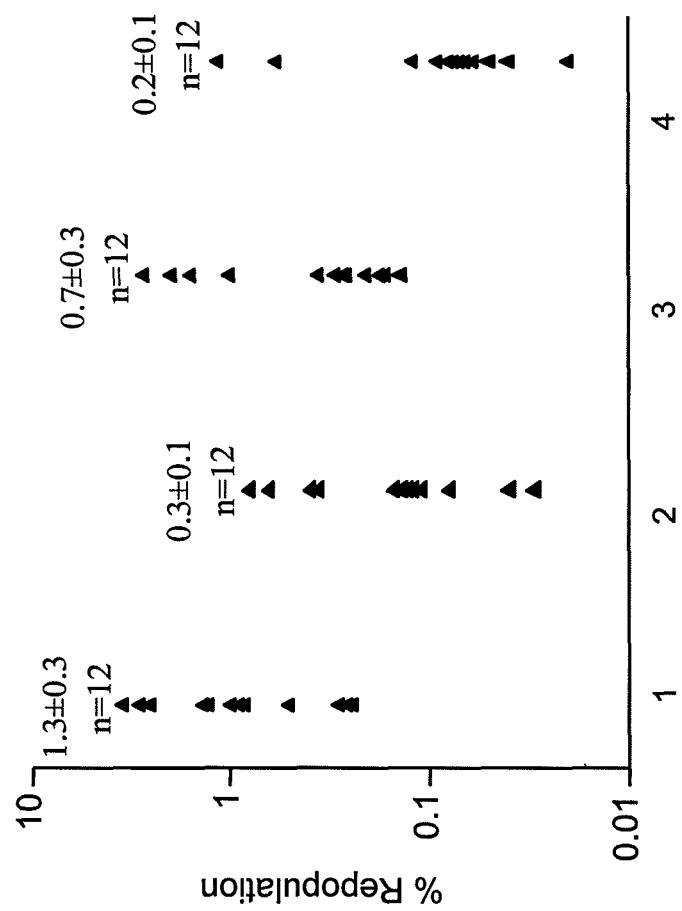
FIG. 5E shows % repopulation of secondary recipients with total hematopoietic (CD45/71$^+$, col. 1), myeloid (CD15/66b$^+$, col. 2), B-lymphoid (CD34−CD19/20$^+$, col. 3), and primitive (CD34$^+$, col. 5) human cells, transplanted with bone marrow from the primary mice transplanted with cultured in STF medium containing Angptl5 and IGFBP-2 (lane 4 of FIG. 5B) and transplanted into sublethally irradiated secondary recipients.

To measure the self-renewal potential of SCID-repopulating cells (SRCs), bone marrow was collected from the primary mice transplanted with uncultured cells (lane 2 of FIG. 5B) or cells cultured in STF medium containing Angptl5 and IGFBP-2 (lane 4 of FIG. 5B) and transplanted them into sublethally irradiated secondary recipients. Bone marrow aspirate from one hind leg from a primary recipient was used to transplant two secondary recipients. Multilineage engraftment in secondary NOD/SCID recipients was assayed at 5-8 weeks post-transplant (n=12 mice transplanted). While uncultured cells could not engraft secondary recipients (not shown), the cultured cells, again, showed positive engraftment after secondary transplantation (FIG. 5E). These data indicate a net expansion of human HSCs during the initial culture period. Two additional independent experiments demonstrated that human HSCs were dramatically expanded in culture using the methods described herein.

Limiting Dilution Analysis of Human Cord Blood CD133+ Cells Transplanted into NOD/SCID Mice after Culture at Normal or Low Oxygen Levels.

Figure 6A:
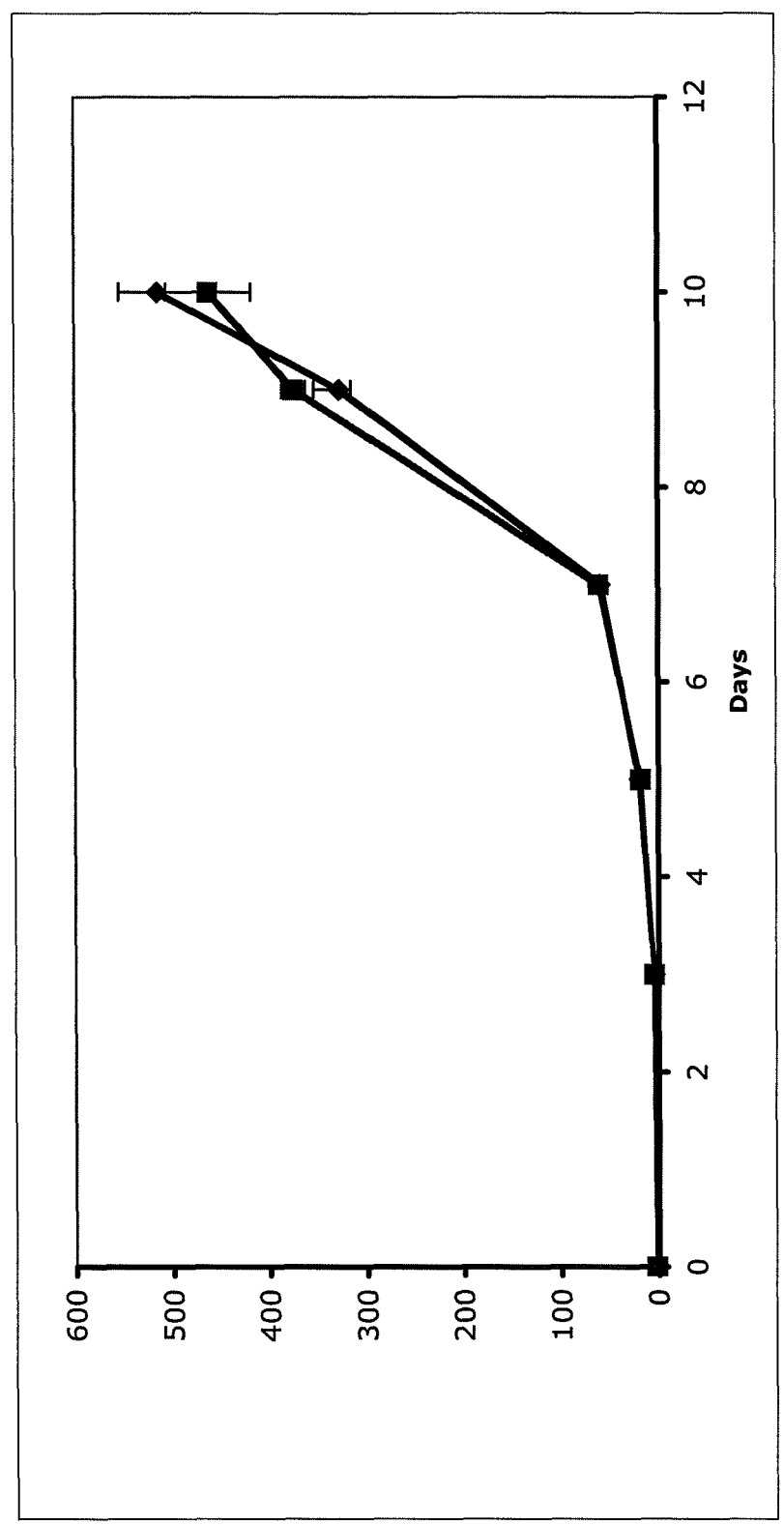
FIG. 6A shows total cell number over time of $2 \times 10^5$ human cord blood CD133$^+$ cells in STF medium containing Angptl5 and IGFBP-2 cultured in low levels of $O_2$ (diamonds) and normal levels of $O_2$ (squares).
Figure 6B:
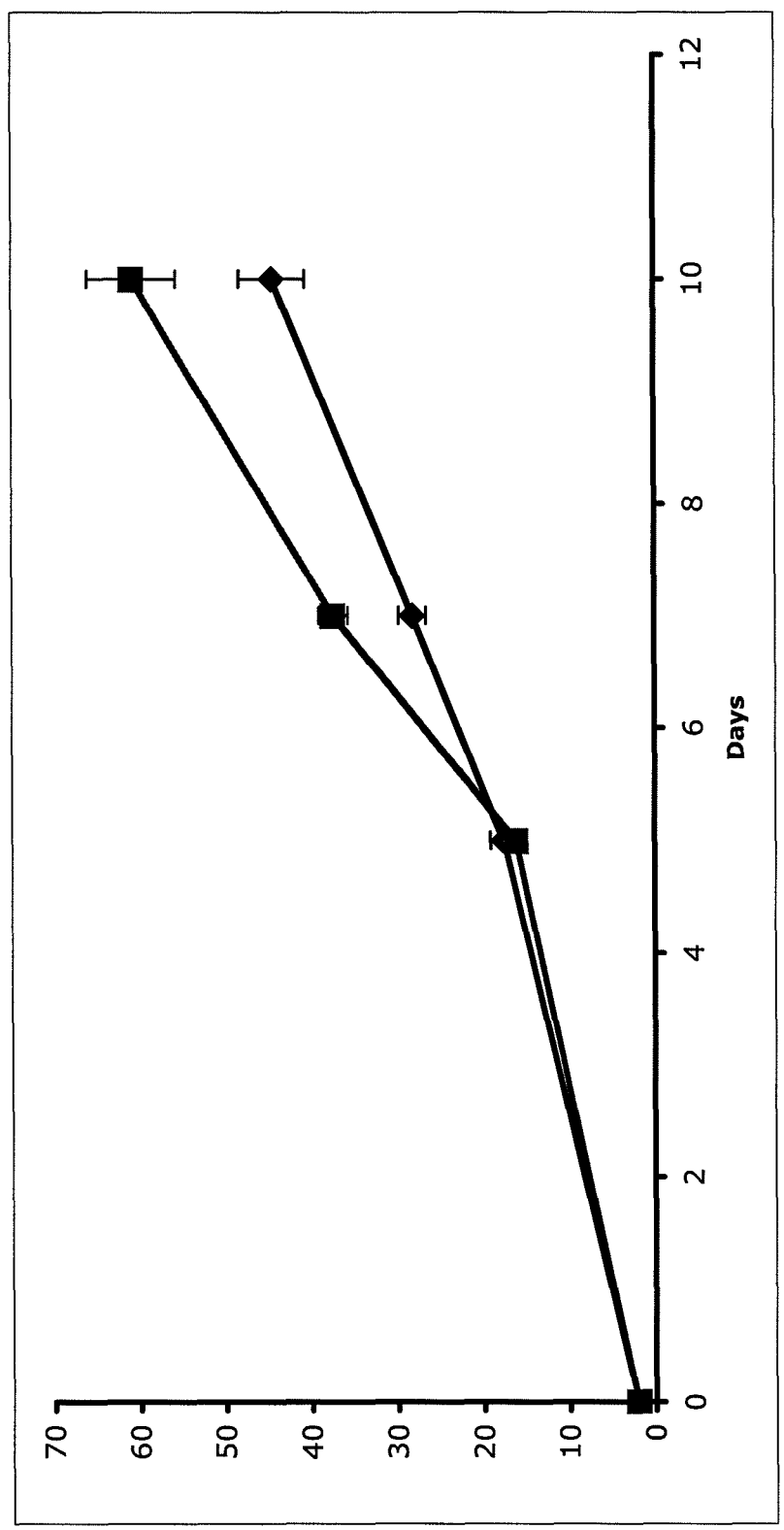
FIG. 6B shows the number of CD34$^+$ primitive cells over time for human HSCs cultured in STF medium containing Angptl5 and IGFBP-2 cultured in low levels of $O_2$ (diamonds) and normal levels of $O_2$ (squares).

The culture system provided herein dramatically expands human SRCs as demonstrated by several additional independent experiments. In one representative experiment, $2 \times 10^5$ human cord blood CD133+ cells were cultured in STF medium containing 500 ng/ml Angptl5 and 100 ng/ml IGFBP-2 under normal or low $O_2$ conditions. The numbers of total cells (FIG. 6A) and CD34+ cells (FIG. 6B) were counted. After 10 days of culture, the number of total cells in these two conditions did not differ significantly and both increased greater than 200 fold (FIG. 6A). Nevertheless, a higher number of CD34+ primitive cells was observed after 5 days of culture at normal $O_2$ versus low $O^2$ (FIG. 6B).

Figure 6C:
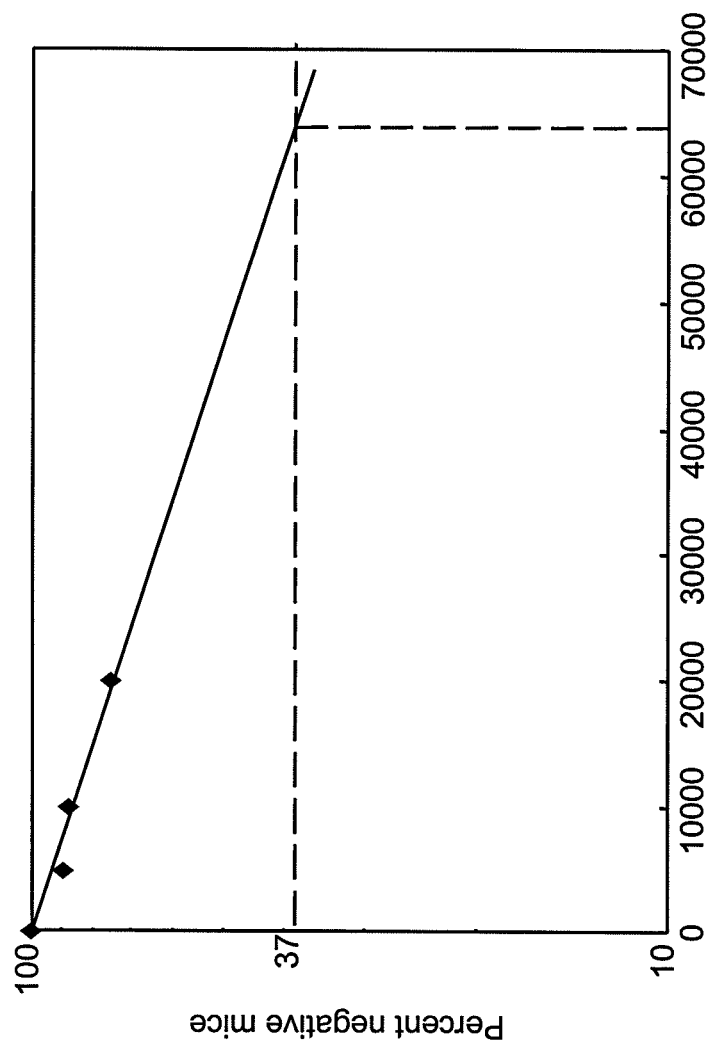
FIG. 6C shows limiting dilution analysis of the repopulating ability of cells before culture.
Figure 6D:
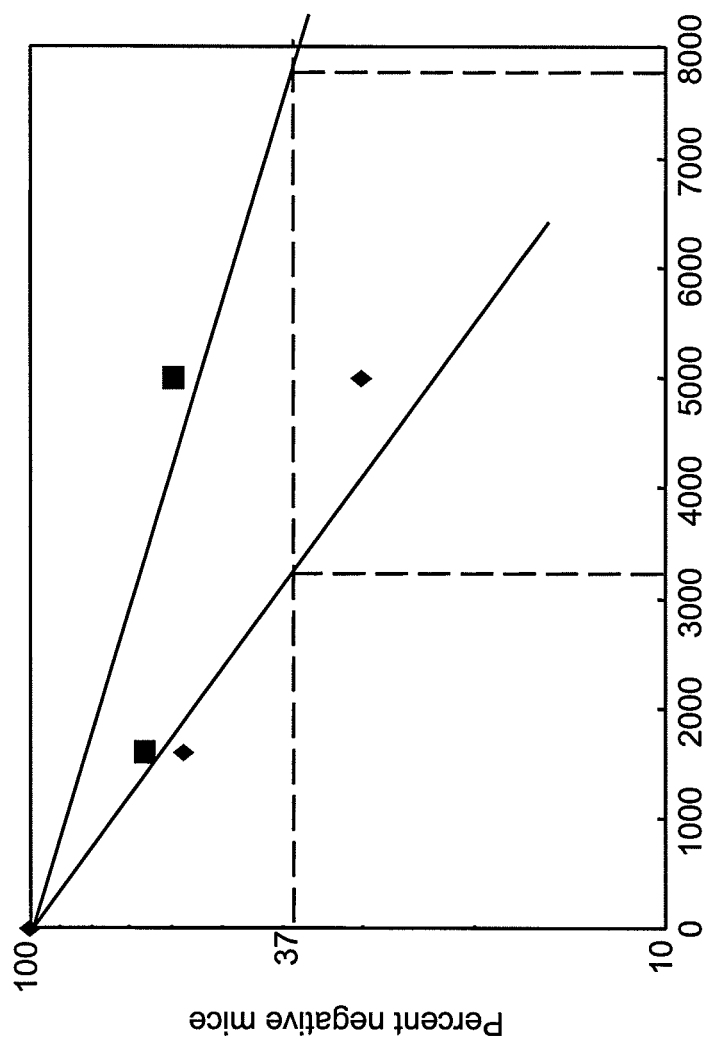
FIG. 6D shows limiting dilution analysis of the repopulating ability of cells after culture for 10 days in STF medium containing 500 ng/ml of Angptl5 and 100 ng/ml IGFBP-2 in low levels of $O_2$ (squares) and normal levels of $O_2$ (diamonds).

Limiting dilution assays were performed to quantitate the SRC frequencies before (FIG. 6C) and after (FIG. 6D) culture. As demonstrated in FIGS. 6B and 6C, after a 10-day culture, the number of SRCs cultured in serum-free STF medium containing Angptl5 and IGFBP-2 at low or normal $O_2$ increased by 8- or 20-fold, respectively. Plotted is the percentage of recipient mice containing less than 1% human hematopoietic populations in recipient mouse bone marrow 6-8 weeks after transplant versus the number of input or input-equivalent cells injected. The progeny of 10,000 input cells cultured at normal or low $O_2$ repopulated all recipients and these data points (zero percent negative mice) are not plotted. The frequency of repopulating cells (CRU) for this particular sample of uncultured CD133+ cells is 1 per 64,075 cells (95% confidence interval for mean: 1/23,919 to 1/171,643, n=25). That is, as calculated from Poisson statistics, injection of on average of 64,075 uncultured human CD133+ cells is sufficient to repopulate 63% (=1-1/e) of transplanted mice. When cells were cultured in STF medium containing Angptl5 and IGFBP-2 at low $O_2$, the CRU frequency was 1/7,814 input equivalent cells (95% confidence interval for mean: 1/3,432 to 1/17,791, n=26), ~8 fold greater than that of the uncultured cells. Strikingly, when the cells were cultured at normal $O_2$, the CRU frequency increased to 1/3,209 input equivalent cells (95% confidence interval for mean: 1/1,889 to 1/5,453, n=27). This indicates that the total number of functional SRCs increased ~20 fold.

FIG. 6E shows multilineage engraftment in NOD/SCID recipients transplanted with 20,000 uncultured CD133+ cells (left panel, n=8) or cultured progeny from 5,000 initial CD133+ cells at normal $O_2$ (right panel, n=10). Some mice transplanted with uncultured cells had zero percent donor repopulation and these data points are not plotted. (total hematopoietic (cols. 1, and 5, CD45/71+), myeloid (cols. 2 and 6, CD15/66b+), B-lymphoid (cols. 3 and 7, CD34− CD19/20+), and primitive (cols. 4 and 8 CD34+) lineages are shown. (* Value is significantly different from the value of the uncultured cells. Student's t-test, p<0.05.) As demonstrated in FIG. 6E, these cultured cells had much greater levels of multi-lineage engraftment than uncultured cells.

It has been suggested that hypoxia improves expansion of human SRCs. (Danet, et al., *J Clin Invest* 112, 126-35 (2003)). As demonstrated herein, profound expansion of SRCs was observed in a hypoxia condition. Unexpectedly, the SRC expansion was even greater under normoxic pressure.

Human cord blood CD34+ cells cultured in the presence of Angptl5 and IGFBP-2 also achieved expansion of SRCs (data not shown).

The use of Angptls and IGFBP-2 for the ex vivo expansion of human HSCs allows increased clinical use of cord blood for bone marrow transplantation because human HSCs can now be expanded ex vivo in a defined medium. The technology provided herein will be useful for the development of novel strategies of cell and gene therapies that utilize HSCs.

Angiopoietin 2

Competitive Reconstitution Analysis

Figure 7:
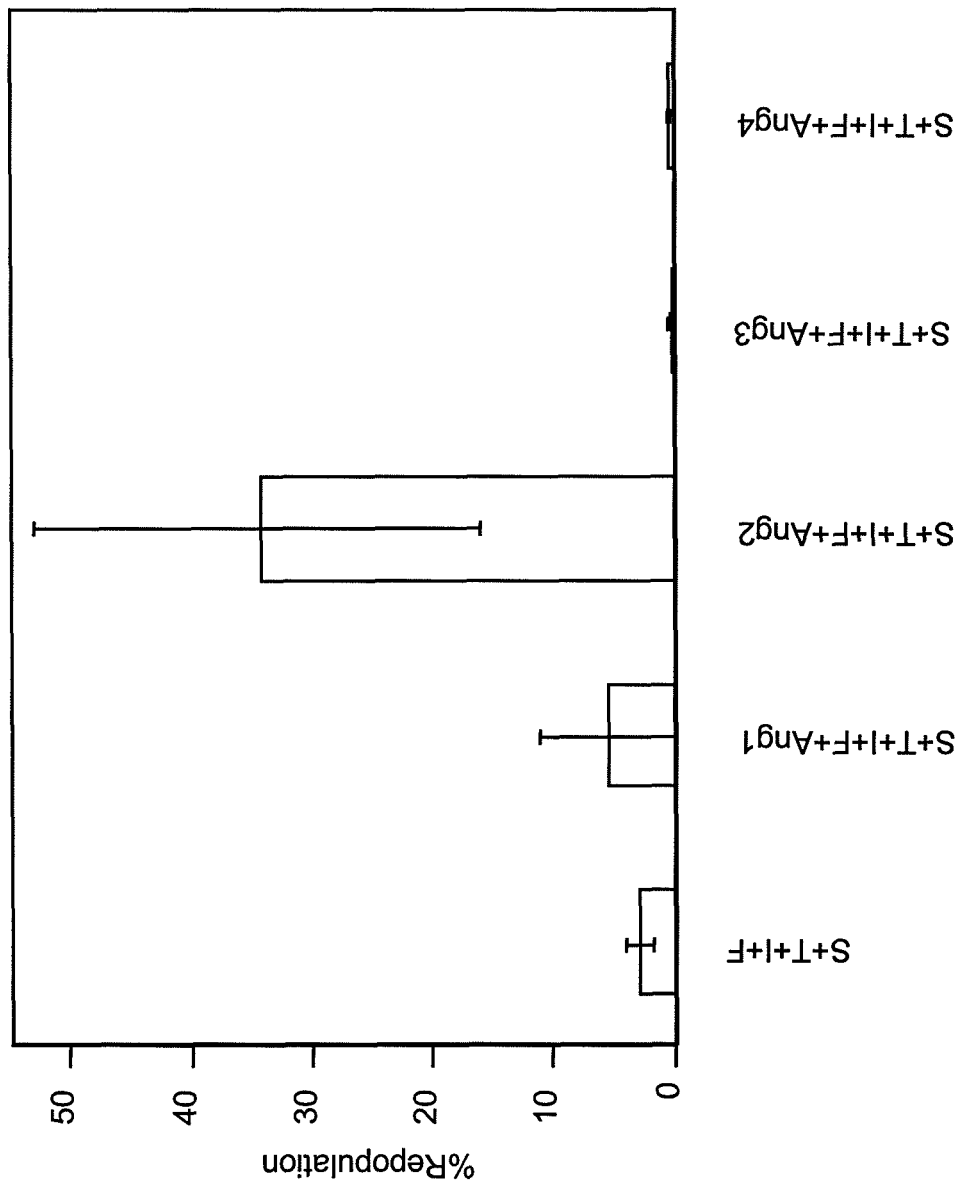
FIG. 7 is a bar graph showing percent repopulation 4 months after transplant with 20 CD45.2 bone marrow SP Sca-1$^+$ CD45$^+$ cells cultured in STIF medium with angiopoietin 2 together with $1 \times 10^5$ CD45.1 bone marrow cells into CD45.1 recipients (n=4-5).

Twenty CD45.2 donor cells were cultured for 10 d in serum-free conditioned STIF medium or in the same medium with 500 ng/ml purified human angiopoietin 1, human angiopoietin 2, mouse angiopoietin 3, or human angiopoietin 4. The cells cotransplanted with $1 \times 10^5$ freshly isolated CD45.1 competitor bone marrow cells, into recipient mice. The mixture injected intravenously via the retro-orbital route into each of a group of 6-9 week old CD45.1 mice previously irradiated with a total dose of 10 Gy. Reconstitution 4 months post transplant was measured. To measure reconstitution of transplanted mice, peripheral blood was collected at the indicated times post-transplant and the presence of CD45.1+ and CD45.2+ cells in lymphoid and myeloid compartments were measured as described (Zhang, C. C. and Lodish, H. F. Blood 105, 4314-20 (2005)). Briefly, peripheral blood cells were collected by retro-orbital bleeding, followed by lysis of red blood cells and staining with anti-CD45.2-FITC, and anti-CD45.1-PE, or anti-Thy1.2-PE (for T-lymphoid lineage), anti-B220-PE (for B-lymphoid lineage), anti-Mac-1-PE, anti-Gr-1-PE (cells costaining with anti-Mac-1 and anti-Gr-1 were deemed the myeloid lineage), or anti-Ter119-PE (for erythroid lineage) monoclonal antibodies (BD Pharmingen). As shown in the FIG. 7, angiopoietin 2 stimulates ex vivo expansion of HSCs.

Methods

Mice.

C57 BL/6 CD45.2 and CD45.1 mice were purchased from the Jackson Laboratory or the National Cancer Institute. NOD/SCID (NOD.CB17-Prkdcscid/J) mice were purchased from the Jackson Laboratory and were maintained at the Whitehead Institute animal facility. All animal experiments were performed with the approval of M.I.T. Committee on Animal Care.

Culture Medium.

Serum-free STIF medium is StemSpan serum-free medium (StemCell Technologies) supplemented with 10 μg/ml heparin (Sigma), 10 ng/ml mouse SCF, 20 ng/ml mouse TPO, 20 ng/ml mouse IGF-2 (all from R&D Systems), and 10 ng/ml human FGF-1 (Invitrogen). Serum-free STF medium is the same medium without IGF-2. Indicated amounts of purified Angptl3 (a gift from R&D Systems), Angptl5 (Abnova, Taiwan), or IGFBP-2 (R&D Systems) were added. Conditioned medium was collected from confluent 293T or 3T3 cells after overnight culture.

Mouse HSC Culture.

Twenty BM SP Sca-1+CD45+ cells isolated from 8-10 week old C57BL/6 CD45.2 mice were plated in one well of a U-bottom 96-well plate (3799; Corning) with 160 μl of indicated medium. Cells were cultured at 37° C. in 5% $CO_2$ and normal $O_2$. For the purpose of competitive transplantation, cells were pooled from at least 6 culture wells and mixed with competitors before the indicated numbers of cells were transplanted into each mouse.

Human Cell Culture.

Human total cord blood mononuclear cells were purchased from Cambrex. Cells were plated at $1 \times 10^6$ cells/ml of STIF medium, with 100 ng/ml Angptl3 or Angptl5. Medium volume was increased by adding fresh medium at day 5, 8, 12, 15, and 18 to maintain cell densities at $5 \times 10^5$-$1.5 \times 10^6$ cells/ml. Cells were cultured at 37° C. in 5% $CO_2$ and normal $O_2$. Human cyropreserved cord blood CD133+ cells used in the experiments of FIGS. 5 and 6 were purchased from Cambrex and StemCell Technologies Inc. Cells were plated at 1×10⁴ cells/well in one well of a U-bottom 96-well plate (3799; Corning) with 200 µl of the indicated medium for 2 days. At day 3, cells were pooled from individual wells and transferred to 6-well plates at 5×10⁴ cells/ml. Fresh medium was added at days 4 and 7 to keep the cell density at 2×10⁵ cells/ml (day 4) or 7×10⁵/ml (day 7). Cells were cultured at 37° C. in 5% $CO_2$, and normal $O_2$ or 5% $O_2$ (low $O_2$) levels.

NOD/SCID Transplant.

Uncultured or cultured progeny of human total cord blood mononuclear cells or $CD133^+$ cells at indicated days were collected and injected intravenously via the retro-orbital route into sub-lethally irradiated (350 rad) NOD/SCID mice. Six to eight weeks or at indicated time after transplantation, bone marrow nucleated cells from transplanted animals were analyzed by flow cytometry for the presence of human cells. For secondary transplantations, bone marrow aspirates from one hind leg of a primary recipient were used to transplant two secondary recipients, as described. (Hogan, et al., *Proc Natl Acad Sci USA* 99, 413-8 (2002)). Calculation of CRUs in limiting dilution experiments was conducted using L-Calc software (StemCell Technologies). (Zhang, et al., *Proc Natl Acad Sci USA* 103, 2184-9 (2006)). Mice were considered to be positive for human HSC engraftment when at least 1% (for primary transplantation) or 0.1% (for secondary transplantation) $CD45/71^+$ human cells were detected among the mouse bone marrow cells.

Flow Cytometry.

Donor bone marrow cells were isolated from 8-10 week old C57BL/6 CD45.2 mice. SP $Sca-1^+CD45^+$ cells were isolated as described Zhang, C. C. et al., Nat Med 12, 240-5 (2006). For analyzing repopulation of mouse HSCs, peripheral blood cells of recipient CD45.1 mice were collected by retro-orbital bleeding, followed by lysis of red blood cells and staining with anti-CD45.2-FITC, and anti-CD45.1-PE, or anti-Thy1.2-PE (for T-lymphoid lineage), anti-B220-PE (for B-lymphoid lineage), anti-Mac-1-PE, anti-Gr-1-PE (cells costaining with anti-Mac-1 and anti-Gr-1 were deemed the myeloid lineage), or anti-Ter119-PE (for erythroid lineage) monoclonal antibodies (BD Pharmingen). The "Percent repopulation" shown in all Figures except FIG. 1B was based on the staining results of anti-CD45.2-FITC and anti-CD45.1-PE. In all cases FACS analysis of the above listed lineages was also performed to confirm multilineage reconstitution.

For analyzing human hematopoietic engraftment in NOD/SCID mice, a published protocol was followed. (Cashman, et al., *J Exp Med* 196, 1141-9 (2002)). Briefly, bone marrow cells from recipient NOD/SCID mice were stained with anti-human CD45-PE, CD71-PE, CD15-FITC, and CD66b-FITC to quantify the total human hematopoietic ($CD45/71^+$) cell population as well as the subset of exclusively granulopoietic ($CD15/66b^+$) cells within this population. Cells were stained with anti-human CD34-FITC and anti-human CD19-PE and CD20-PE to quantify human progenitor ($CD34^+$) and B-lineage ($CD34^-CD19/20^+$) populations. In the experiment of FIG. 1, only total human hematopoietic ($CD45/71^+$) engraftment was measured. Anti-human CD34-FITC was used to quantitate $CD34^+$ cells in culture. All anti-human antibodies were purchased from Becton Dickinson.

FACS Sorting.

Donor bone marrow cells were isolated from 8-10 week old C57BL/6 CD45.2 mice. To sort SP $Sca-1^+ CD45^+$ cells, adult mouse bone marrow SP cells (stained as previously described (Zhang, C. C. and Lodish, H. F., Blood 103, 2513-21 (2004); Zhang, C. C. and Lodish, H. F., Blood 105, 4314-20 (2005)) were further stained with anti-Sca-1-PE and anti-CD45-FITC followed by cell sorting on a MoFlo® sorter.

Competitive Reconstitution Analysis.

The indicated numbers of mouse CD45.2 donor cells were mixed with 1×10⁵ freshly isolated CD45.1 competitor bone marrow cells, and the mixture injected intravenously via the retro-orbital route into each of a group of 6-9 week old CD45.1 mice previously irradiated with a total dose of 10 Gy. To measure reconstitution of transplanted mice, peripheral blood was collected at the indicated times post-transplant and the presence of $CD45.1^+$ and $CD45.2^+$ cells in lymphoid and myeloid compartments were measured as described (Zhang, C. C. and Lodish, H. F. *Blood* 103, 2513-21 (2004), Zhang, C. C. and Lodish, H. F., *Blood* (2005)). Calculation of CRUs in limiting dilution experiments was conducted using L-Calc software (StemCell Technologies) (Zhang, et al., *Proc Natl Acad Sci USA* 103, 2184-9 (2006)).

Western blots. Purified proteins or crude proteins in conditioned medium were analyzed by electrophoresis on 4-12% NuPage Bis-Tris polyacrylamide gels (Invitrogen), and proteins were electroblotted onto nitrocellulose membranes. The membranes were probed with anti-human IGFBP-2 polyclonal antibody (AF674, R&D Systems) at 0.1 µg/ml, followed with the horseradish peroxidase-conjugated donkey-anti-goat antibody and detected by a chemiluminescence kit (Millipore).

While the technology has been particularly shown and described with reference to specific embodiments, it should be understood by those skilled in the art that various changes in form and detail may be made therein without departing from the spirit and scope of the technology as defined by the appended claims.

We claim:

1. A method of expanding hematopoietic stem cell numbers comprising incubating human cells in a defined culture medium comprising isolated insulin growth factor binding protein 2 (IGFBP-2), an angiopoietin-like protein (Angptl), and at least one growth factor selected from the group consisting of fibroblast growth factor 1 (FGF-1), thrombopoietin (TPO), and stem cell factor (SCF), wherein at least one of the human cells is a hematopoietic stem cell (HSC).

2. The method of claim 1, wherein the isolated IGFBP-2 is present at a concentration of about 1.0 ng/mL to about 5 µg/mL.

3. The method of claim 1, wherein the isolated IGFBP-2 is recombinantly produced.

4. The method of claim 1, wherein the human cells are cultured for at least five days.

5. The method of claim 1, wherein the human cells are incubated for at least ten days.

6. The method of claim 1, wherein the Angptl is selected from the group consisting of Angptl 3 and Angptl5.

7. The method of claim 1, wherein the culture medium comprises FGF-1, TPO and SCF.

8. The method of claim 1, wherein the at least one additional growth factor is present at a concentration of about 0.5 ng/mL to about 5 µg/mL.

9. The method of claim 1, wherein the human cells are selected from the group consisting of bone marrow cells, peripheral blood cells, umbilical cord blood cells, and fetal liver cells.

10. The method of claim 1, further comprising the step of selecting said HSC by a method comprising selecting one or more primary human cells that express CD133.

11. The method of claim 1, further comprising the step of selecting said HSC by a method comprising selecting one or more primary human cells that express CD34.

12. A method of increasing human hematopoietic stem cell numbers in vitro comprising incubating human cells for at least five days in a defined culture medium comprising isolated insulin growth factor binding protein 2 (IGFBP-2), angiopoietin-like protein 5 (Angptl5), fibroblast growth factor 1 (FGF-1), thrombopoietin (TPO), and stem cell factor (SCF), wherein at least one of the human cells is a hematopoietic stem cell.

13. A method of administering hematopoietic stem cells to an individual comprising:
   a) obtaining human cells from the individual or a donor, wherein at least one of the human cells is a hematopoietic stem cell (HSC);
   b) incubating the human cells in a defined culture medium comprising an isolated insulin growth factor binding protein 2 (IGFBP-2), an angiopoietin-like protein (Angptl), and at least one growth factor selected from the group consisting of fibroblast growth factor 1 (FGF-1), thrombopoietin (TPO), and stem cell factor (SCF), and
   c) transplanting the cultured cells into the individual.

14. The method of claim 13, wherein the isolated IGFBP-2 is present at a concentration of about 1.0 ng/mL to about 5 µg/ml.

15. The method of claim 14, wherein the isolated IGFBP-2 is recombinantly produced.

16. The method of claim 13, wherein the Angptl is selected from the group consisting of Angptl 3 and Angptl5.

17. The method of claim 16, wherein the Angptl is recombinantly produced.

18. The method of claim 13, wherein the human cells are selected from the group consisting of bone marrow cells, peripheral blood cells, umbilical cord blood cells, and fetal liver cells.

19. The method of claim 13, further comprising the step of selecting said HSC by a method comprising selecting one or more primary human cells that express CD133.

20. The method of claim 13, further comprising the step of selecting said HSC by a method comprising selecting one or more primary human cells that express CD34.

* * * * *

SEQUENCE LISTING

```
<160> NUMBER OF SEQ ID NOS: 7

<210> SEQ ID NO 1
<211> LENGTH: 496
<212> TYPE: PRT
<213> ORGANISM: Homo sapiens

<400> SEQUENCE: 1

Met Trp Gln Ile Val Phe Phe Thr Leu Ser Cys Asp Leu Val Leu Ala
 1               5                  10                  15

Ala Ala Tyr Asn Asn Phe Arg Lys Ser Met Asp Ser Ile Gly Lys Lys
            20                  25                  30
```

```
Gln Tyr Gln Val Gln His Gly Ser Cys Ser Tyr Thr Phe Leu Leu Pro
             35                  40                  45

Glu Met Asp Asn Cys Arg Ser Ser Ser Pro Tyr Val Ser Asn Ala
 50                  55                  60

Val Gln Arg Asp Ala Pro Leu Glu Tyr Asp Asp Ser Val Gln Arg Leu
 65                  70                  75                  80

Gln Val Leu Glu Asn Ile Met Glu Asn Asn Thr Gln Trp Leu Met Lys
             85                  90                  95

Leu Glu Asn Tyr Ile Gln Asp Asn Met Lys Lys Glu Met Val Glu Ile
            100                 105                 110

Gln Gln Asn Ala Val Gln Asn Gln Thr Ala Val Met Ile Glu Ile Gly
            115                 120                 125

Thr Asn Leu Leu Asn Gln Thr Ala Glu Gln Thr Arg Lys Leu Thr Asp
130                 135                 140

Val Glu Ala Gln Val Leu Asn Gln Thr Thr Arg Leu Glu Leu Gln Leu
145                 150                 155                 160

Leu Glu His Ser Leu Ser Thr Asn Lys Leu Glu Lys Gln Ile Leu Asp
                165                 170                 175

Gln Thr Ser Glu Ile Asn Lys Leu Gln Asp Lys Asn Ser Phe Leu Glu
            180                 185                 190

Lys Lys Val Leu Ala Met Glu Asp Lys His Ile Ile Gln Leu Gln Ser
            195                 200                 205

Ile Lys Glu Glu Lys Asp Gln Leu Gln Val Leu Val Ser Lys Gln Asn
210                 215                 220

Ser Ile Ile Glu Glu Leu Glu Lys Lys Ile Val Thr Ala Thr Val Asn
225                 230                 235                 240

Asn Ser Val Leu Gln Lys Gln Gln His Asp Leu Met Glu Thr Val Asn
                245                 250                 255

Asn Leu Leu Thr Met Met Ser Thr Ser Asn Ser Ala Lys Asp Pro Thr
            260                 265                 270

Val Ala Lys Glu Glu Gln Ile Ser Phe Arg Asp Cys Ala Glu Val Phe
            275                 280                 285

Lys Ser Gly His Thr Thr Asn Gly Ile Tyr Thr Leu Thr Phe Pro Asn
290                 295                 300

Ser Thr Glu Glu Ile Lys Ala Tyr Cys Asp Met Glu Ala Gly Gly Gly
305                 310                 315                 320

Gly Trp Thr Ile Ile Gln Arg Arg Glu Asp Gly Ser Val Asp Phe Gln
                325                 330                 335

Arg Thr Trp Lys Glu Tyr Lys Val Gly Phe Gly Asn Pro Ser Gly Glu
            340                 345                 350

Tyr Trp Leu Gly Asn Glu Phe Val Ser Gln Leu Thr Asn Gln Gln Arg
            355                 360                 365

Tyr Val Leu Lys Ile His Leu Lys Asp Trp Glu Gly Asn Glu Ala Tyr
370                 375                 380

Ser Leu Tyr Glu His Phe Tyr Leu Ser Ser Glu Glu Leu Asn Tyr Arg
385                 390                 395                 400

Ile His Leu Lys Gly Leu Thr Gly Thr Ala Gly Lys Ile Ser Ser Ile
                405                 410                 415

Ser Gln Pro Gly Asn Asp Phe Ser Thr Lys Asp Gly Asp Asn Asp Lys
            420                 425                 430

Cys Ile Cys Lys Cys Ser Gln Met Leu Thr Gly Gly Trp Trp Phe Asp
            435                 440                 445

Ala Cys Gly Pro Ser Asn Leu Asn Gly Met Tyr Tyr Pro Gln Arg Gln
450                 455                 460
```

```
Asn Thr Asn Lys Phe Asn Gly Ile Lys Trp Tyr Tyr Trp Lys Gly Ser
465                 470                 475                 480

Gly Tyr Ser Leu Lys Ala Thr Thr Met Met Ile Arg Pro Ala Asp Phe
                485                 490                 495

<210> SEQ ID NO 2
<211> LENGTH: 328
<212> TYPE: PRT
<213> ORGANISM: Homo sapiens

<400> SEQUENCE: 2

Met Leu Pro Arg Val Gly Cys Pro Ala Leu Pro Leu Pro Pro Pro
 1               5                  10                  15

Leu Leu Pro Leu Leu Pro Leu Leu Leu Leu Leu Gly Ala Ser Gly
                20                  25                  30

Gly Gly Gly Gly Ala Arg Ala Glu Val Leu Phe Arg Cys Pro Pro Cys
            35                  40                  45

Thr Pro Glu Arg Leu Ala Ala Cys Gly Pro Pro Arg Val Ala Pro Pro
        50                  55                  60

Ala Ala Val Ala Ala Val Ala Gly Gly Ala Arg Met Pro Cys Ala Glu
65                  70                  75                  80

Leu Val Arg Glu Pro Gly Cys Gly Cys Cys Ser Val Cys Ala Arg Leu
                85                  90                  95

Glu Gly Glu Ala Cys Gly Val Tyr Thr Pro Arg Cys Gly Gln Gly Leu
            100                 105                 110

Arg Cys Tyr Pro His Pro Gly Ser Glu Leu Pro Leu Gln Ala Leu Val
        115                 120                 125

Met Gly Glu Gly Thr Cys Glu Lys Arg Arg Asp Ala Glu Tyr Gly Ala
130                 135                 140

Ser Pro Glu Gln Val Ala Asp Asn Gly Asp Asp His Ser Glu Gly Gly
145                 150                 155                 160

Leu Val Glu Asn His Val Asp Ser Thr Met Asn Met Leu Gly Gly Gly
                165                 170                 175

Gly Ser Ala Gly Arg Lys Pro Leu Lys Ser Gly Met Lys Glu Leu Ala
            180                 185                 190

Val Phe Arg Glu Lys Val Thr Glu Gln His Arg Gln Met Gly Lys Gly
        195                 200                 205

Gly Lys His His Leu Gly Leu Glu Glu Pro Lys Lys Leu Arg Pro Pro
210                 215                 220

Pro Ala Arg Thr Pro Cys Gln Gln Glu Leu Asp Gln Val Leu Glu Arg
225                 230                 235                 240

Ile Ser Thr Met Arg Leu Pro Asp Glu Arg Gly Pro Leu Glu His Leu
                245                 250                 255

Tyr Ser Leu His Ile Pro Asn Cys Asp Lys His Gly Leu Tyr Asn Leu
            260                 265                 270

Lys Gln Cys Lys Met Ser Leu Asn Gly Gln Arg Gly Glu Cys Trp Cys
        275                 280                 285

Val Asn Pro Asn Thr Gly Lys Leu Ile Gln Gly Ala Pro Thr Ile Arg
        290                 295                 300

Gly Asp Pro Glu Cys His Leu Phe Tyr Asn Glu Gln Glu Ala Arg
305                 310                 315                 320

Gly Val Asp Thr Gln Arg Met Gln
                325

<210> SEQ ID NO 3
```

<211> LENGTH: 491
<212> TYPE: PRT
<213> ORGANISM: Homo sapiens

<400> SEQUENCE: 3

```
Met Lys Thr Phe Thr Trp Thr Leu Gly Val Leu Phe Phe Leu Leu Val
  1               5                  10                  15

Asp Thr Gly His Cys Arg Gly Gly Gln Phe Lys Ile Lys Lys Ile Asn
             20                  25                  30

Gln Arg Arg Tyr Pro Arg Ala Thr Asp Gly Lys Glu Glu Ala Lys Lys
         35                  40                  45

Cys Ala Tyr Thr Phe Leu Val Pro Glu Gln Arg Ile Thr Gly Pro Ile
     50                  55                  60

Cys Val Asn Thr Lys Gly Gln Asp Ala Ser Thr Ile Lys Asp Met Ile
 65                  70                  75                  80

Thr Arg Met Asp Leu Glu Asn Leu Lys Asp Val Leu Ser Arg Gln Lys
                 85                  90                  95

Arg Glu Ile Asp Val Leu Gln Leu Val Val Asp Val Asp Gly Asn Ile
            100                 105                 110

Val Asn Glu Val Lys Leu Leu Arg Lys Glu Ser Arg Asn Met Asn Ser
        115                 120                 125

Arg Val Thr Gln Leu Tyr Met Gln Leu Leu His Glu Ile Ile Arg Lys
    130                 135                 140

Arg Asp Asn Ser Leu Glu Leu Ser Gln Leu Glu Asn Lys Ile Leu Asn
145                 150                 155                 160

Val Thr Thr Glu Met Leu Lys Met Ala Thr Arg Tyr Arg Glu Leu Glu
                165                 170                 175

Val Lys Tyr Ala Ser Leu Thr Asp Leu Val Asn Asn Gln Ser Val Met
            180                 185                 190

Ile Thr Leu Leu Glu Glu Gln Cys Leu Arg Ile Phe Ser Arg Gln Asp
        195                 200                 205

Thr His Val Ser Pro Pro Leu Val Gln Val Val Pro Gln His Ile Pro
    210                 215                 220

Asn Ser Gln Gln Tyr Thr Pro Gly Leu Leu Gly Gly Asn Glu Ile Gln
225                 230                 235                 240

Arg Asp Pro Gly Tyr Pro Arg Asp Leu Met Pro Pro Asp Leu Ala
                245                 250                 255

Thr Ser Pro Thr Lys Ser Pro Phe Lys Ile Pro Pro Val Thr Phe Ile
                260                 265                 270

Asn Glu Gly Pro Phe Lys Asp Cys Gln Gln Ala Lys Glu Ala Gly His
            275                 280                 285

Ser Val Ser Gly Ile Tyr Met Ile Lys Pro Glu Asn Ser Asn Gly Pro
    290                 295                 300

Met Gln Leu Trp Cys Glu Asn Ser Leu Asp Pro Gly Gly Trp Thr Val
305                 310                 315                 320

Ile Gln Lys Arg Thr Asp Gly Ser Val Asn Phe Phe Arg Asn Trp Glu
                325                 330                 335

Asn Tyr Lys Lys Gly Phe Gly Asn Ile Asp Gly Glu Tyr Trp Leu Gly
            340                 345                 350

Leu Glu Asn Ile Tyr Met Leu Ser Asn Gln Asp Asn Tyr Lys Leu Leu
        355                 360                 365

Ile Glu Leu Glu Asp Trp Ser Asp Lys Lys Val Tyr Ala Glu Tyr Ser
    370                 375                 380

Ser Phe Arg Leu Glu Pro Glu Ser Glu Phe Tyr Arg Leu Arg Leu Gly
385                 390                 395                 400
```

```
Thr Tyr Gln Gly Asn Ala Gly Asp Ser Met Met Trp His Asn Gly Lys
            405                 410                 415

Gln Phe Thr Thr Leu Asp Arg Asp Lys Asp Met Tyr Ala Gly Asn Cys
            420                 425                 430

Ala His Phe His Lys Gly Gly Trp Trp Tyr Asn Ala Cys Ala His Ser
            435                 440                 445

Asn Leu Asn Gly Val Trp Tyr Arg Gly Gly His Tyr Arg Ser Lys His
            450                 455                 460

Gln Asp Gly Ile Phe Trp Ala Glu Tyr Arg Gly Gly Ser Tyr Ser Leu
465                 470                 475                 480

Arg Ala Val Gln Met Met Ile Lys Pro Ile Asp
            485                 490

<210> SEQ ID NO 4
<211> LENGTH: 493
<212> TYPE: PRT
<213> ORGANISM: Homo sapiens

<400> SEQUENCE: 4

Met Arg Pro Leu Cys Val Thr Cys Trp Trp Leu Gly Leu Leu Ala Ala
1               5                   10                  15

Met Gly Ala Val Ala Gly Gln Glu Asp Gly Phe Glu Gly Thr Glu Glu
            20                  25                  30

Gly Ser Pro Arg Glu Phe Ile Tyr Leu Asn Arg Tyr Lys Arg Ala Gly
        35                  40                  45

Glu Ser Gln Asp Lys Cys Thr Tyr Thr Phe Ile Val Pro Gln Gln Arg
    50                  55                  60

Val Thr Gly Ala Ile Cys Val Asn Ser Lys Glu Pro Glu Val Leu Leu
65                  70                  75                  80

Glu Asn Arg Val His Lys Gln Glu Leu Glu Leu Leu Asn Asn Glu Leu
                85                  90                  95

Leu Lys Gln Lys Arg Gln Ile Glu Thr Leu Gln Gln Leu Val Glu Val
            100                 105                 110

Asp Gly Gly Ile Val Ser Glu Val Lys Leu Leu Arg Lys Glu Ser Arg
        115                 120                 125

Asn Met Asn Ser Arg Val Thr Gln Leu Tyr Met Gln Leu Leu His Glu
130                 135                 140

Ile Ile Arg Lys Arg Asp Asn Ala Leu Glu Leu Ser Gln Leu Glu Asn
145                 150                 155                 160

Arg Ile Leu Asn Gln Thr Ala Asp Met Leu Gln Leu Ala Ser Lys Tyr
                165                 170                 175

Lys Asp Leu Glu His Lys Tyr Gln His Leu Ala Thr Leu Ala His Asn
            180                 185                 190

Gln Ser Glu Ile Ile Ala Gln Leu Glu Glu His Cys Gln Arg Val Pro
        195                 200                 205

Ser Ala Arg Pro Val Pro Gln Pro Pro Ala Ala Pro Pro Arg Val
210                 215                 220

Tyr Gln Pro Pro Thr Tyr Asn Arg Ile Ile Asn Gln Ile Ser Thr Asn
225                 230                 235                 240

Glu Ile Gln Ser Asp Gln Asn Leu Lys Val Leu Pro Pro Pro Leu Pro
                245                 250                 255

Thr Met Pro Thr Leu Thr Ser Leu Pro Ser Ser Thr Asp Lys Pro Ser
            260                 265                 270

Gly Pro Trp Arg Asp Cys Leu Gln Ala Leu Glu Asp Gly His Asp Thr
        275                 280                 285
```

```
Ser Ser Ile Tyr Leu Val Lys Pro Glu Asn Thr Asn Arg Leu Met Gln
    290                 295                 300

Val Trp Cys Asp Gln Arg His Asp Pro Gly Gly Trp Thr Val Ile Gln
305                 310                 315                 320

Arg Arg Leu Asp Gly Ser Val Asn Phe Phe Arg Asn Trp Glu Thr Tyr
                325                 330                 335

Lys Gln Gly Phe Gly Asn Ile Asp Gly Glu Tyr Trp Leu Gly Leu Glu
            340                 345                 350

Asn Ile Tyr Trp Leu Thr Asn Gln Gly Asn Tyr Lys Leu Leu Val Thr
        355                 360                 365

Met Glu Asp Trp Ser Gly Arg Lys Val Phe Ala Glu Tyr Ala Ser Phe
    370                 375                 380

Arg Leu Glu Pro Glu Ser Glu Tyr Tyr Lys Leu Arg Leu Gly Arg Tyr
385                 390                 395                 400

His Gly Asn Ala Gly Asp Ser Phe Thr Trp His Asn Gly Lys Gln Phe
                405                 410                 415

Thr Thr Leu Asp Arg Asp His Asp Val Tyr Thr Gly Asn Cys Ala His
            420                 425                 430

Tyr Gln Lys Gly Gly Trp Trp Tyr Asn Ala Cys Ala His Ser Asn Leu
        435                 440                 445

Asn Gly Val Trp Tyr Arg Gly Gly His Tyr Arg Ser Arg Tyr Gln Asp
450                 455                 460

Gly Val Tyr Trp Ala Glu Phe Arg Gly Gly Ser Tyr Ser Leu Lys Lys
465                 470                 475                 480

Val Val Met Met Ile Arg Pro Asn Pro Asn Thr Phe His
                485                 490

<210> SEQ ID NO 5
<211> LENGTH: 460
<212> TYPE: PRT
<213> ORGANISM: Homo sapiens

<400> SEQUENCE: 5

Met Phe Thr Ile Lys Leu Leu Leu Phe Ile Val Pro Leu Val Ile Ser
  1               5                  10                  15

Ser Arg Ile Asp Gln Asp Asn Ser Ser Phe Asp Ser Leu Ser Pro Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
        50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175
```

```
Asp Leu Leu Gln Thr Val Glu Asp Gln Tyr Lys Gln Leu Asn Gln Gln
            180                 185                 190

His Ser Gln Ile Lys Glu Ile Glu Asn Gln Leu Arg Arg Thr Ser Ile
        195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
        275                 280                 285

Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 6
<211> LENGTH: 406
<212> TYPE: PRT
<213> ORGANISM: Homo sapiens

<400> SEQUENCE: 6

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
        35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95
```

-continued

```
Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
        115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
        195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240

Trp Glu Ala Tyr Lys Ala Gly Phe Gly Asp Pro His Gly Glu Phe Trp
                245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
        275                 280                 285

Phe Ser Val His Leu Gly Gly Glu Asp Thr Ala Tyr Ser Leu Gln Leu
    290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
                325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
        355                 360                 365

Gln Gln Arg Gln Lys Leu Lys Lys Gly Ile Phe Trp Lys Thr Trp Arg
    370                 375                 380

Gly Arg Tyr Tyr Pro Leu Gln Ala Thr Thr Met Leu Ile Gln Pro Met
385                 390                 395                 400

Ala Ala Glu Ala Ala Ser
                405

<210> SEQ ID NO 7
<211> LENGTH: 388
<212> TYPE: PRT
<213> ORGANISM: Homo sapiens

<400> SEQUENCE: 7

Met Met Ser Pro Ser Gln Ala Ser Leu Leu Phe Leu Asn Val Cys Ile
  1               5                  10                  15

Phe Ile Cys Gly Glu Ala Val Gln Gly Asn Cys Val His His Ser Thr
                 20                  25                  30

Asp Ser Ser Val Val Asn Ile Val Glu Asp Gly Ser Asn Ala Lys Asp
             35                  40                  45

Glu Ser Lys Ser Asn Asp Thr Val Cys Lys Glu Asp Cys Glu Glu Ser
         50                  55                  60
```

-continued

```
Cys Asp Val Lys Thr Lys Ile Thr Arg Glu Glu Lys His Phe Met Cys
 65              70                  75                  80

Arg Asn Leu Gln Asn Ser Ile Val Ser Tyr Thr Arg Ser Thr Lys Lys
                 85                  90                  95

Leu Leu Arg Asn Met Met Asp Glu Gln Gln Ala Ser Leu Asp Tyr Leu
                100                 105                 110

Ser Asn Gln Val Asn Glu Leu Met Asn Arg Val Leu Leu Leu Thr Thr
                115                 120                 125

Glu Val Phe Arg Lys Gln Leu Asp Pro Phe Pro His Arg Pro Val Gln
        130                 135                 140

Ser His Gly Leu Asp Cys Thr Asp Ile Lys Asp Thr Ile Gly Ser Val
145                 150                 155                 160

Thr Lys Thr Pro Ser Gly Leu Tyr Ile Ile His Pro Glu Gly Ser Ser
                165                 170                 175

Tyr Pro Phe Glu Val Met Cys Asp Met Asp Tyr Arg Gly Gly Gly Trp
            180                 185                 190

Thr Val Ile Gln Lys Arg Ile Asp Gly Ile Ile Asp Phe Gln Arg Leu
            195                 200                 205

Trp Cys Asp Tyr Leu Asp Gly Phe Gly Asp Leu Leu Gly Glu Phe Trp
        210                 215                 220

Leu Gly Leu Lys Lys Ile Phe Tyr Ile Val Asn Gln Lys Asn Thr Ser
225                 230                 235                 240

Phe Met Leu Tyr Val Ala Leu Glu Ser Glu Asp Asp Thr Leu Ala Tyr
                245                 250                 255

Ala Ser Tyr Asp Asn Phe Trp Leu Glu Asp Glu Thr Arg Phe Phe Lys
            260                 265                 270

Met His Leu Gly Arg Tyr Ser Gly Asn Ala Gly Asp Ala Phe Arg Gly
            275                 280                 285

Leu Lys Lys Glu Asp Asn Gln Asn Ala Met Pro Phe Ser Thr Ser Asp
    290                 295                 300

Val Asp Asn Asp Gly Cys Arg Pro Ala Cys Leu Val Asn Gly Gln Ser
305                 310                 315                 320

Val Lys Ser Cys Ser His Leu His Asn Lys Thr Gly Trp Trp Phe Asn
                325                 330                 335

Glu Cys Gly Leu Ala Asn Leu Asn Gly Ile His His Phe Ser Gly Lys
                340                 345                 350

Leu Leu Ala Thr Gly Ile Gln Trp Gly Thr Trp Thr Lys Asn Asn Ser
            355                 360                 365

Pro Val Lys Ile Lys Ser Val Ser Met Lys Ile Arg Arg Met Tyr Asn
    370                 375                 380

Pro Tyr Phe Lys
385
```